(12) United States Patent
Kulp et al.

(10) Patent No.: US 6,690,472 B2
(45) Date of Patent: Feb. 10, 2004

(54) PULSED LASER LINESCANNER FOR A BACKSCATTER ABSORPTION GAS IMAGING SYSTEM

(75) Inventors: Thomas J. Kulp, Livermore, CA (US); Thomas A. Reichardt, Livermore, CA (US); Randal L. Schmitt, Tijeras, NM (US); Ray P. Bambha, Martinez, CA (US)

(73) Assignee: Sandia National Laboratories, Livermore, CA (US)

( * ) Notice: Subject to any disclaimer, the term of this patent is extended or adjusted under 35 U.S.C. 154(b) by 226 days.

(21) Appl. No.: 09/965,527

(22) Filed: Sep. 26, 2001

(65) Prior Publication Data

US 2002/0071122 A1 Jun. 13, 2002

Related U.S. Application Data

(60) Provisional application No. 60/236,924, filed on Sep. 28, 2000.

(51) Int. Cl.$^7$ ............................................... G01N 21/47
(52) U.S. Cl. ................................. 356/437; 250/330
(58) Field of Search .............................. 356/437, 438; 250/334, 338.5, 330; 358/474, 482, 483; 348/166, 203

(56) References Cited

U.S. PATENT DOCUMENTS

| | | | | |
|---|---|---|---|---|
| 4,555,627 A | * | 11/1985 | McRae, Jr. ................. 250/334 |
| 4,772,789 A | * | 9/1988 | Maram et al. ............... 250/330 |
| 5,430,293 A | * | 7/1995 | Sato et al. .................. 250/330 |
| 5,523,569 A | * | 6/1996 | Hornfeld et al. ............ 250/330 |
| 5,656,813 A | * | 8/1997 | Moore et al. ............... 250/330 |
| 5,982,511 A | * | 11/1999 | Sato ............................ 358/475 |

* cited by examiner

Primary Examiner—Richard A. Rosenberger
(74) Attorney, Agent, or Firm—Timothy P. Evans

(57) ABSTRACT

An active (laser-illuminated) imaging system is described that is suitable for use in backscatter absorption gas imaging (BAGI). A BAGI imager operates by imaging a scene as it is illuminated with radiation that is absorbed by the gas to be detected. Gases become "visible" in the image when they attenuate the illumination creating a shadow in the image. This disclosure describes a BAGI imager that operates in a linescanned manner using a high repetition rate pulsed laser as its illumination source. The format of this system allows differential imaging, in which the scene is illuminated with light at least 2 wavelengths—one or more absorbed by the gas and one or more not absorbed. The system is designed to accomplish imaging in a manner that is insensitive to motion of the camera, so that it can be held in the hand of an operator or operated from a moving vehicle.

39 Claims, 21 Drawing Sheets

FIG. 10A Side View

FIG. 10B Front View

PULSED LASER LINESCANNER FOR A BACKSCATTER ABSORPTION GAS IMAGING SYSTEM

STATEMENT OF PRIORITY

This following application for patent seeks priority to co-pending U.S. Patent Provisional Application Ser. No. 60/236,924, filed on Sep. 28, 2000, and herein claims the benefit thereto.

STATEMENT OF GOVERNMENT INTEREST

The United States Government has rights in this invention pursuant to Contract No. DE-AC04-94AL85000 between the United States Department of Energy and Sandia Corporation for the operation of Sandia National Laboratories.

BACKGROUND OF THE INVENTION

1. Field of the Invention

The present invention relates to systems for performing backscatter absorption gas imaging (BAGI), and more specifically, it relates to a pulsed linescanner for use in BAGI imaging.

2. Description of Related Art

BAGI is an existing and patented technique disclosed in U.S. Pat. No. 4,555,627, titled "Backscatter absorption gas imaging system". Simply stated, the patent covers the use of infrared laser-illuminated imaging for the remote video visualization of gas plumes. It describes the coupling of an infrared laser to an infrared camera to produce an instrument that views a scene in the infrared as the laser illuminates the scene. The system produces, therefore, a laser-illuminated video picture of the scene. If a gas plume is present that can absorb light at the center wavelength, it creates a shadow in the picture that is essentially a video image of the gas plume. BAGI is currently being commercialized by Laser Imaging Systems (LIS), which offers systems operating in the 9–11 $\mu$m wavelength range based on the use of $CO_2$ lasers.

U.S. Pat. No. 3,317,730 discloses a method for determining atmospheric pollution by the detection of backscattered modulated infrared radiation.

U.S. Pat. No. 3,832,548 to Wallack shows a general infrared absorption detector in which infrared radiation first passes through a filter means having a plurality of positions for transmitting selected wavelengths, and then passes through a sample cell to a detector.

U.S. Pat. No. 4,204,121 to Milly shows a mobile detector comprising a vertical sampling array for quantifying emission rates from pollution sources.

U.S. Pat. No. 4,264,209 to Brewster shows a system for producing an indication of a concentration of a gas of interest in which the gas is illuminated and the output is filtered alternately with two filters, one at an absorption band of a gas to be detected, the other at a passband outside the absorption band.

U.S. Pat. No. 4,262,199 to Bridges, et al., shows a mobile infrared target detection and recognition system including an assembly of infrared detection elements which scan a field of view to produce a signal representative of the infrared level from point to point.

U.S. Pat. No. 3,829,694 to Goto discloses apparatus for detecting gases or particles using Mie scattering of pulsed light beams to detect resonance absorption.

U.S. Pat. No. 3,517,190 to Astheimer discloses a method for monitoring stack effluent from a remote position by illuminating the effluent across a broad spectral band and detecting the reflected illumination in two spectral regions: one in an absorption band and one outside the absorption band to determine the quantity of absorbing gas from the signal ratio.

The publication Kulp et al., "Development of a pulsed backscatter-absorption gas-imaging system and its application to the visualization of natural gas leaks", Appl. Opt. 37 3912–3922 (1998), describes the development of a pulsed BAGI imager that uses full-field illumination at a laser pulse repetition rate of 30 Hz.

The publication Powers et al. "Demonstration of differential backscatter absorption gas imaging", Appl. Opt. 39 1440–1448 (2000) described the development of a pulsed BAGI imager that uses full-field illumination at a laser repetition rate of 30 Hz and is capable of differential detection. It operates in a way that is adversely affected by system motion.

The publication of Imeshev et al. "Lateral patterning of nonlinear frequency conversion with transversely varying quasi-phase-matching gratings" Optics Letters 23 673–675 (1998) describes the use of periodically poled lithium niobate with lateral patterning to produce second harmonic frequency output beam with a flat-topped spatial profile.

SUMMARY OF THE INVENTION

It is an object of the present invention to provide a pulsed linescanner for use in a backscatter absorption gas imaging (BAGI) system.

It is another object of the invention to provide a BAGI imager that is capable of operation with pulsed laser sources. The term "laser" is intended to include lasers as well as any other light sources with spectral and brightness properties meeting the requirements presented in this teaching. For example such lightsources could include a laser followed by a frequency conversion device or an incandescent beam from a gas discharge source.

It is another object of the invention to provide a pulsed linescanner that is capable of differential imaging.

It is another object of the invention to provide methods for acquisition of images by a pulsed linescanner in ways that are immune to moderate camera motion (such as might be encountered in hand-held or vehicle-mounted operation).

It is another object of the invention to provide methods for acquisition of images by a pulsed differential linescanner in ways that are immune to moderate camera motion (such as might be encountered in hand-held or vehicle-mounted operation).

It is another object of the invention to provide means for achieving a linescanning BAGI imager that is capable of both single-wavelength and differential imaging.

It is another object of the invention to provide a pulsed linescanned imager that by concentrating the transmitted light in a small number of rows achieves a higher backscattered signal from a given target using a given laser pulse energy and repetition rate than can be obtained by a system employing full-field illumination.

These and other objects of the invention will be apparent to those skilled in the art based on the teachings herein.

The present invention is an active (laser illuminated) imaging system that is suitable for use as a BAGI imager. As in all BAGI systems, the present invention employs a laser, tuned to a wavelength absorbed by the gas to be detected, that is coupled to a suitable video camera. The laser illuminates the scene as the camera images it. Gases present in the imaged scene are visualized when they absorb the laser light, thus creating a dark region in the video picture. This allows the imager to be used to rapidly detect and pinpoint leaks of gases (such as hydrocarbons found in leaks at petroleum refineries or in natural gas pipelines) that absorb light produced by the laser employed. To maximize the attenuation, the spectral profile of the laser must be narrower than the target gas absorption linewidth and must be centered at the peak of the strongest absorption line that is not affected by interfering species. Operation away from the peak of the gas absorption or with lasers having a broader spectral width than the absorption feature is also possible with an associated reduction in detection sensitivity.

The invention described here uses a pulsed laser as its illumination source and creates images by linescanning. Plume visualization is accomplished in either of two modes—termed single-wavelength imaging and differential imaging. In single-wavelength imaging the scene is illuminated only with laser radiation having a wavelength absorbed by the gas. The gas image is produced when the gas plume attenuates the backscatter return from solid objects in the imaged scene. In differential imaging, the scene is illuminated by radiation at two different wavelengths; one strongly absorbed by the gas, termed the "on-wavelength", and one that is not absorbed (or weakly absorbed), termed the "off-wavelength". For every displayed frame, a backscatter signal is collected from each scene pixel at each wavelength. An image generated from the on-wavelength backscatter would be identical to the previously described single-wavelength image. An image generated from the off-wavelength backscatter would, on the other hand, contain no gas image (or only a weak gas image). In differential imaging both the on-and off-wavelength signals are processed to generate a differential image, in which the differences between the two frames are emphasized. An example of such processing is the log-ratio, where the logarithm of the ratio of the on-wavelength signal to the off-wavelength signal is displayed. The two wavelengths are selected to be close enough together that the reflectivities of the target scene surfaces are nearly identical at each wavelength. Thus, ideally, the on-wavelength and off-wavelength return signals differ from one another only in regions of the scene that are occluded by the gas plume. Ideally, differential processing by the log-ratio approach will produce an image containing only the gas plume image and no elements of the scene image. This will allow the plume image to be displayed at high contrast, which eases its visual recognition. Additionally, quantitative measurements of path-integrated gas concentration can be made following a calibration of the differential absorption signal. It is also within the skill of the art to overlay the differential-mode image of the gas plume on a passive video image of the scene to assist in identifying the location of the gas plume.

The present invention differs from that described in the original BAGI patent (U.S. Pat. No. 4,555,627). The system description in the original patent specified use of a cw laser emitting light of a single frequency whose beam was raster-scanned across the target. Thus, it was only useful for single-wavelength imaging and could not achieve the additional sensitivity provided by differential imaging. Also, the requirement for a cw beam restricts the choice of laser that can be used for gas imaging, as some operate only in a pulsed mode. This is often true for lasers that use nonlinear mixing to generate light of a particular output frequency because the efficiency of the nonlinear mixing process scales with the peak power of the light field used to pump the nonlinear crystal. Pulsed lasers can create output pulses of high peak power. Thus, a BAGI approach employing a pulsed format offers additional choice of lasers to use for gas imaging and, thus, more choice of wavelengths and other relevant attributes (compactness, portability, ruggedness, efficiency). This is important because there are no lasers currently available in pulsed or cw formats that are suitable for BAGI and are tunable over all wavelengths of interest for gas detection. The ability to operate in a pulsed mode allows operation in some important wavelength ranges (e.g., tunable operation in the 8–12 $\mu$m range, which coincides with the molecular fingerprint region) in which there are no broadly-tunable cw lasers available.

The present invention differs from previous disclosures of pulsed BAGI imaging systems and differential pulsed BAGI imaging systems. In the publication Kulp et al. discussed above, a pulsed BAGI imager is described that uses a 30-Hz-repetition-rate-laser to illuminate the full field-of-view of a two-dimensional infrared focal-plane array camera. In the publication Powers et al. described above, that approach is extended to allow differential imaging in a manner in which the collection of on-wavelength frames is interleaved with that of off-wavelength frames—thus an on-wavelength frame is collected 1/30th of a second after an off-wavelength frame. Pairs of on-wavelength and off-wavelength frames are processed to generate log-ratio differential image frames at a rate of 15 Hz. The time between on- and off-wavelength frames is long relative to the timescale of movement of the camera, objects in the scene, or of the plume itself. Thus, a difficulty that occurs in practical use of the published system is misregistration between the on- and off-wavelength pixels, leading to significant errors in the differential image. These limitations can preclude operation in certain important modes in which movement occurs, such as when the system is handheld by an operator (such as for roaming inspection by an operator in a refinery), or when it is operated from a moving vehicle such as a van (for leak detection from natural gas distribution lines in residential areas) or from a helicopter (for leak detection from natural gas transmission lines in rural areas).

Operation in a linescanned mode is also consistent with the use of high repetition-rate pulsed lasers. "High repetition rate" for the laser is defined as being a rate higher than the image frame rate, which is typically between 10 to 60 Hz. The system described here uses a laser having a several kHz repetition rate, which is a relatively common for diode-pumped solid-state pump lasers. Diode pumped solid-state lasers can have advantageous features including small size and power consumption, and the present invention makes it possible for gas imaging to employ these lasers.

DETAILED DESCRIPTION OF THE INVENTION

System Overview and Requirements

The present invention is a gas-imaging instrument that creates gas-plume images in a linescanned fashion using pulsed-laser illumination. The term "laser" is intended to include lasers as well as any other light sources with spectral and brightness properties meeting the requirements presented in this teaching. For example such lightsources could include a laser followed by a frequency conversion device or an incandescent beam from a gas discharge source. It is capable of operating in a single-wavelength or differential mode and is designed to produce high-quality images even when the system experiences moderate movement or vibration (such as might occur when held in the hands of an operator or driven in a vehicle).

The present imager may be employed for the rapid detection and pinpointing of leaks of gases that absorb at wavelengths within the tuning range of the particular laser used in the system. An example of an embodiment of the invention is a portable BAGI system that is capable of operating at wavelengths (1.3–4.5 µm; particularly 2.8–4.5 µm) that are absorbed by a large number of hydrocarbon vapors (such as are found in leaks at petroleum refineries or in natural gas pipelines). Examples of problems addressable by the system include the detection of fugitive emissions at petroleum refineries, the detection of leaks in natural-gas industry piping and hardware, detection of chemical agent leaks, and testing of the integrity of containers (fuel tanks, radiator coils, etc) that are intentionally filled with a tracer gas that absorbs at the operating wavelength.

Figure 1:
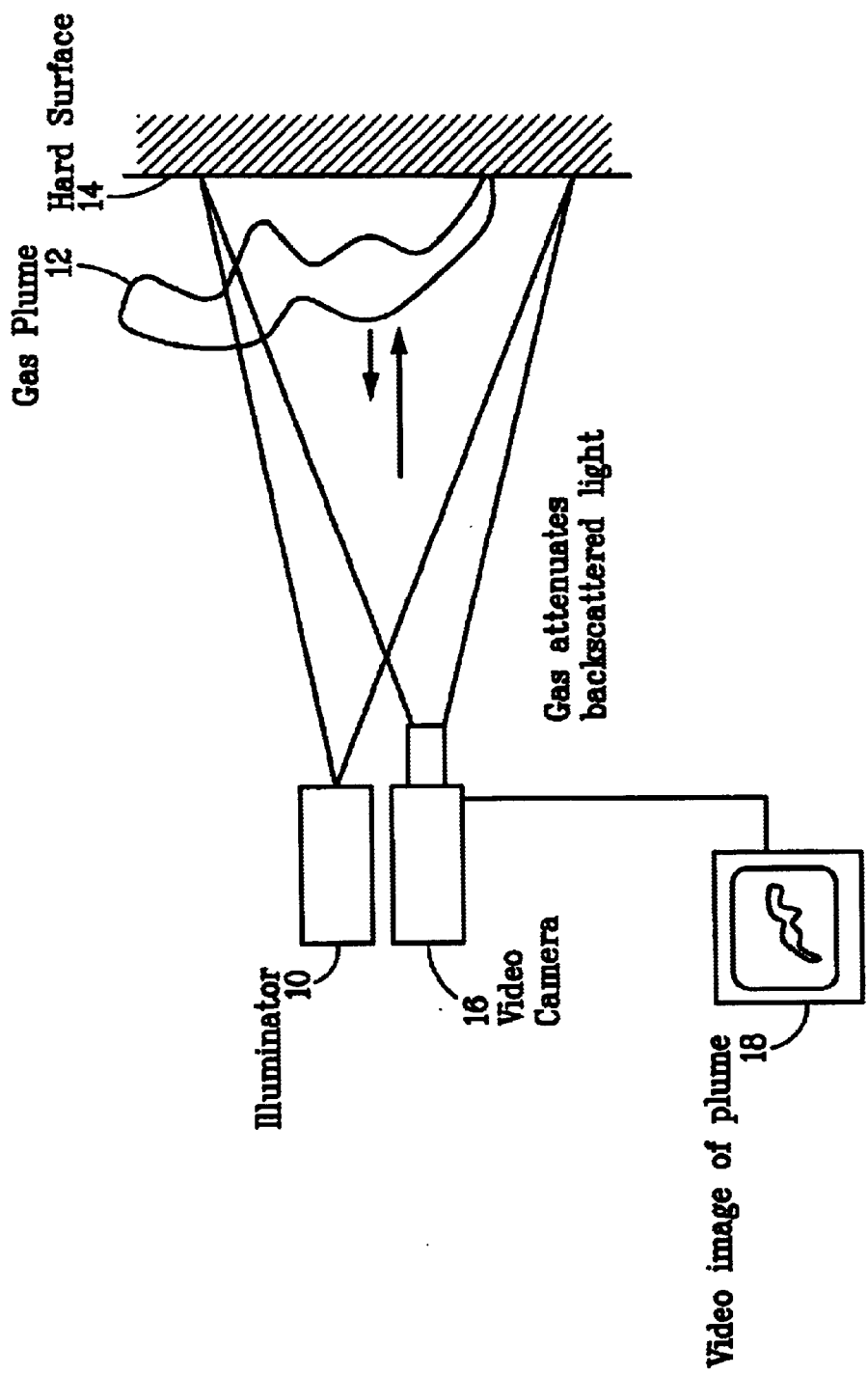
FIG. 1 shows the basic components of a BAGI system—a lightsource that illuminates the scene at a wavelength absorbed by the gas and a camera that images the scene using the backscattered illumination.
Figure 2:
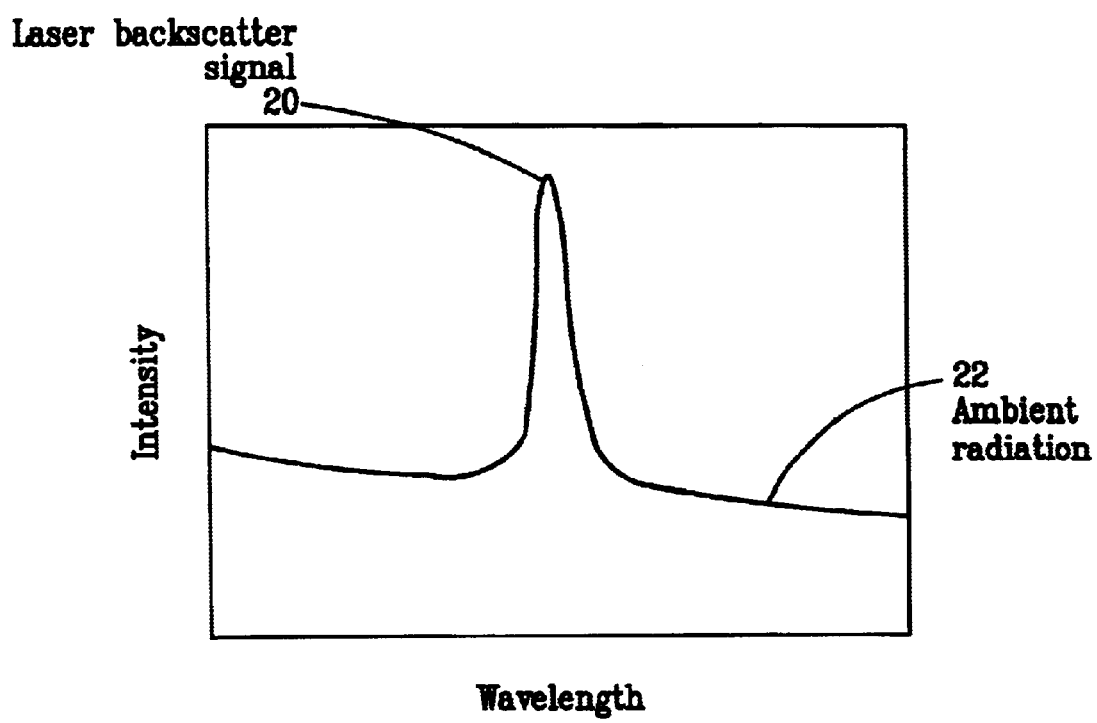
FIG. 2 shows the spectral profile of the signal from the target. It consists of a narrow feature due to the backscatter from the illumination source located on a pedestal of ambient radiation. It is desirable to collect the backscatter signal, which is coincident with the gas absorption, while rejecting the ambient background.

A BAGI system consists of two basic components (FIG. 1)—a lightsource 10 that illuminates the scene (gas plume 12 and hard surface 14) and a camera 16 that images the scene using primarily the backscattered radiation from the illumination source. Because a reasonably strong backscatter signal must be collected in a short ($\sim \leq 1/10$ s) time to allow real-time video display (shown at monitor 18) and with moderate laser power, it is necessary that the backscatter occur from solid objects 14 in the imaged area and not from the atmosphere itself. Gases are visualized when they attenuate the backscattered radiation. One requirement of the BAGI lightsource is that it illuminate the scene at a wavelength that is well absorbed by the gas to be detected while being transmitted efficiently through the atmosphere over the roundtrip distance between the imager and the backscattering surfaces. A requirement of the lightsource-camera combination is that it produce an image of sufficient quality to allow gases to be imaged under the required operating conditions. Referring to FIG. 2, one measure of the image quality is the fraction of the detected light 20 (compared to ambient radiation 22) originating from back-scattered photons at a wavelength absorbed by the gas (FIG. 2). In a single-wavelength image the collection of photons at wavelengths not absorbed by the gas will reduce the contrast of the gas image. In a properly designed system, photons collected at the absorption wavelength originate primarily from backscattered radiation from the illumination source, but there will also be a small component of ambient light 22 from the scene (FIG. 2). Thermal radiation, scattered sunlight, or other sources of ambient radiation can be significant in the infrared. In a differential image the photons collected from the on-wavelength laser pulse and from the off-wavelength laser pulse should also consist primarily of backscattered photons.

Other measures of quality are the signal-to-noise ratio of the image produced and the presentation of the image in a format that can easily be recognized by the operator. In operation, gases are detected by their attenuation of the return signal. If the magnitude of the attenuation is less than or comparable to the noise level in the return signal, the gas-plume image will be imperceptible. Thus, the signal-to-noise ratio of the image must be sufficient to support detection of the minimum attenuation expected. For example, consider a situation in which the minimum gas concentration to be imaged produces a 10% attenuation of the return signal. If the signal-to-noise ratio of the return signal were 10:1, attenuation by the gas would cause a reduction in return signal that is equal to the noise level, making it undetectable. If the signal-to-noise ratio were 30:1, the gas would reduce the return signal by an amount 3 times the noise level, which is often used as a definition of minimum detection level for analytical instrumentation.

The image signal-to-noise ratio requirement is necessary to allow imaging but it may not be sufficient to permit an operator to discern a gas plume. One must also consider the minimum contrast that the eye is capable of visualizing. For single-wavelength imaging, this threshold was previously set at 1 part in 12 of the full greyscale—thus, if a plume is present against a surface that produces a full greyscale (white) return signal, the gas must reduce the return signal to 11/12 of full value to produce a darkening that is perceptible to the operator. If, however, the gas is silhouetted against a darker portion of the imaged scene, a greater attenuation is required to produce visual detection. Coupling the 1 part in 12 attenuation with the 3-to-1 signal-to-noise ratio requirement produces a minimum signal-to-noise ratio requirement of 36 to 1.

Another measure of quality is the immunity of the image signal to moderate motion of the system, the imaged scene, or the plume itself. The system must be able to produce imagery of the plume while experiencing these motions without being subject to image smearing or misregistration of pixels collected at different wavelengths.

Detailed Description and Satisfaction of Requirements

Figure 3:
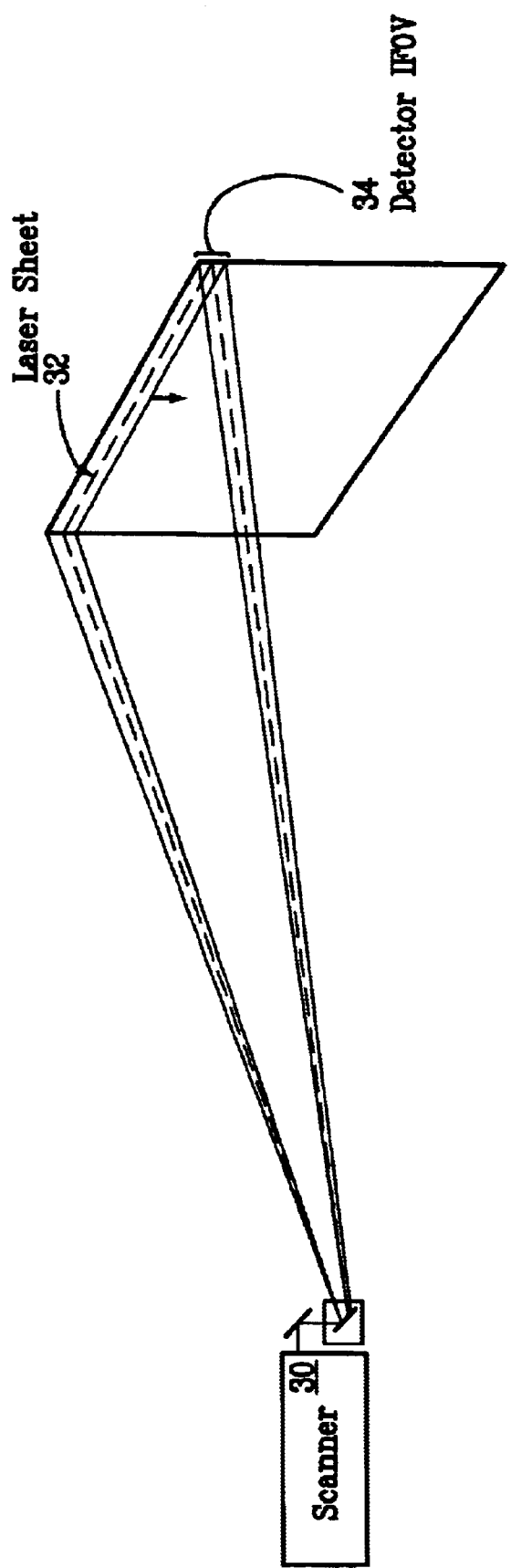
FIG. 3 shows a diagram of a generalized linescanner. The laser beam is formed into a sheet that illuminates a line at the target. The line is contained within the instantaneous filed of view (IFOV) of the detector array.
Figure 4:
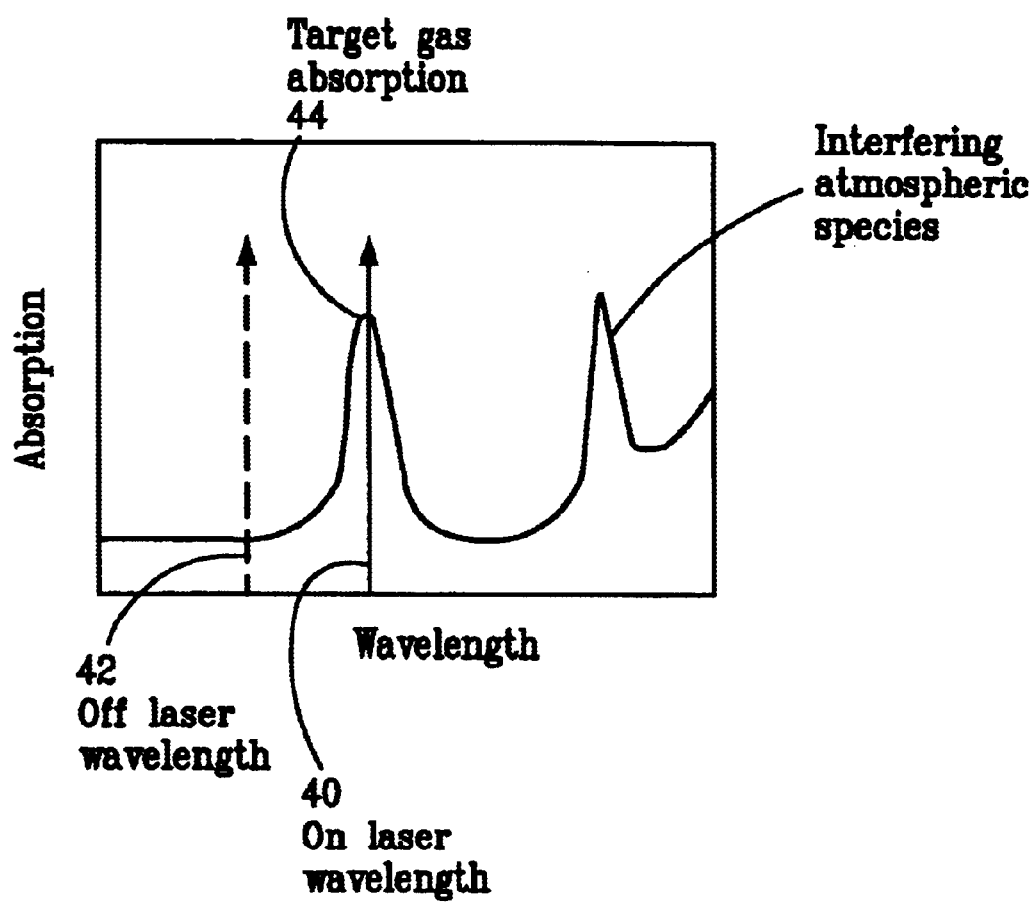
FIG. 4 shows the spectrum of the gas absorption in relationship to the on and off wavelength position of the illuminating laser source.

The present invention meets these requirements by using a linescanned approach in which the illumination source is a pulsed laser. The invention is capable of operating in either single-wavelength or differential mode. FIG. 3 depicts the general notion of a linescanned pulsed imager. Linescanner 30 directs a sheet of laser illumination 32. A linear or two-dimensional detector array instantaneous field of view 34 is used to image one or more lines on the target scene (FIG. 3). A pulsed laser provides a linear illumination pattern that is formatted to illuminate one or more of the viewed lines on the target scene. Thus, the laser line(s) overlap with the instantaneous field-of-view (IFOV) of the linear detector array at the target. To form an image, the intersection zone of the detector IFOV and the laser line is swept up and down the target by one or more mechanically-scanned mirrors, or by an electro-optic or acousto-optic deflection mechanism. As shown in FIG. 4, in single-wavelength imaging, the laser is synchronized to illuminate each image line with a pulse of radiation at the on-wavelength 40, which overlays an exemplary target gas absorption line 44 in the figure. In differential imaging each line must be illuminated with pulses of radiation at both the on- and off-wavelengths (40 and 42 respectively). Electronics process the on- and off-wavelength signals to generate the differential signal. In both modes, data processing electronics in the camera assemble the lines to form a displayable image.

The requirement for illumination that is coincident in wavelength with the gas absorption is met by using an appropriately-tuned laser as the lightsource. Lasers are well suited for use as BAGI illuminators because they emit radiation that is inherently spectrally-bright (i.e., they emit collimated, high power light in a narrow spectral bandwidth). This allows illumination that is spectrally narrower than the absorption features of the gas to be detected (which tend to be narrow for many gases) while maintaining a strong backscatter return signal.

The need to maintain a high ratio of backscatter to ambient radiation is met by temporal, spatial, and spectral suppression of ambient light. Ambient radiation is rejected by one or some combination of three methods: (1) placing a filter in front of the detector array that transmits over a narrow spectral bandwidth centered at the laser frequency (when operating in the thermal IR this should be a cold filter); (2) electronically gating the detector array to integrate signal for a short time window that corresponds to the arrival of the short pulse of laser backscatter photons; and (3) using scanning to limit the dwell time of the detector IFOV on a particular target region. Condition (1) rejects spectrally-broad ambient radiation by spectrally filtering out wavelengths that are not coincident or near-coincident with that of the spectrally-narrow laser. Condition (2) limits ambient radiation collection by integrating only in a short time window around the arrival time of the short-duration laser pulse. Thus, collection of the continuously-arriving ambient radiation is reduced. Condition (3) limits collection of ambient radiation by another form of time gating, in which the dwell time of the IFOV on a particular scene line is shortened by the scanning process. Depending on the relative magnitudes of the scan rate or the integration time, either (2) or (3) will determine the effective temporal window over which light is integrated.

The requirement to produce an image of sufficient signal-to-noise ratio for single-wavelength imaging is met by appropriate design of the laser and optical components of the system. The ability of the present invention to meet the signal-to-noise and visual detection requirements for single-wavelength imaging is demonstrated by modeling performance of a specific embodiment in the next section of this application. The magnitude of the return signal is dependent upon several system parameters, including the laser pulse energy, the roundtrip atmospheric attenuation, the reflectivity of the target surface, the diameter of the optical receiver collection aperture and the lens f-number, the transmission efficiency of the laser transmitter and receiver, and the responsivity and sensitivity of the detector array used.

The present invention further facilitates visual recognition of the plume by allowing differential operation. As in single-wavelength imaging, a contrast of 1 part in 12 must be generated in a differential image to allow visual detection. However, the differential image contains only the gas plume—the background is removed by the log-ratio process. Thus, the signal associated with the plume can be spread over the full greyscale of the display, whereas in single-wavelength imaging, signals from both objects in the scene and the plume are spanned across the greyscale. A bright object in the scene of a single-wavelength image can cause intensities in the remainder of the scene to be compressed, which reduces the gas plume contrast. In differential imaging, it is only necessary that the plume signal-to-noise ratio in the differential image exceed 3 for the plume to be detectable.

Differential imaging also reduces the role of plume motion in its visual detection. Static plumes can be confused with areas of low reflectivity in single wavelength imaging and it is often necessary that the plume move to be unambiguously detected. Because differential imaging removes all features that do not absorb or reflect differently at the two illumination wavelengths, it is much more likely that an object remaining in the differential image is the gas plume, and it is not necessary that it move to be detected. A pulsed differential linescanner that meets the signal-to-noise requirements is shown in the next section.

The requirement for immunity to system motion is met differently for single-wavelength and differential imaging. For single-wavelength imaging, it is met by designing the scanning to occur on a timescale that is fast enough to ensure that pixels in the top row of the image are well-registered with pixels at the bottom row (i.e., there is no smearing of the image as the camera is moved). The speed required to prevent smearing depends upon the movements of the camera, plume, and scene objects expected in a particular system embodiment. For a handheld imager, a frame rate of 10 Hz has been used as the minimum acceptable value. In a raster-scanned imager, Laser Imaging Systems has shown that operation at 10 Hz reduces smearing to an acceptable level. In the description of the specific embodiment, it is demonstrated that operation at >10 Hz (23 Hz) can be achieved for single-wavelength imaging.

For differential imaging, the present invention is designed to avoid image smearing, spatial misregistration of the on- and off-wavelength pixels, and systematic biases. The requirements to meet these conditions are described as follows:

1. The return signal should be scaled for the energy of the laser pulse transmitted if pulse-to-pulse energy fluctuations represent a significant noise source.
2. Good temporal and spatial registration of the on- and off-wavelength pixels must be achieved. The time between collection of on and off wavelength pixels in a given frame must be small enough to avoid loss of spatial registration due to motion of the camera or of the plume.
3. The use of the same line of detectors for both on- and off-wavelength measurements is preferable to avoid errors caused by pixel nonuniformity; however, non-uniformity correction should be performed if the same line of detectors cannot be used.
4. The laser line illumination should be sufficiently homogeneous to create a uniform image.

The first condition is met by employing a separate detector to monitor the energy of each outgoing pulse. The image return signal is then scaled to this energy prior to differential processing, thus normalizing out the energy fluctuations.

Figure 5:
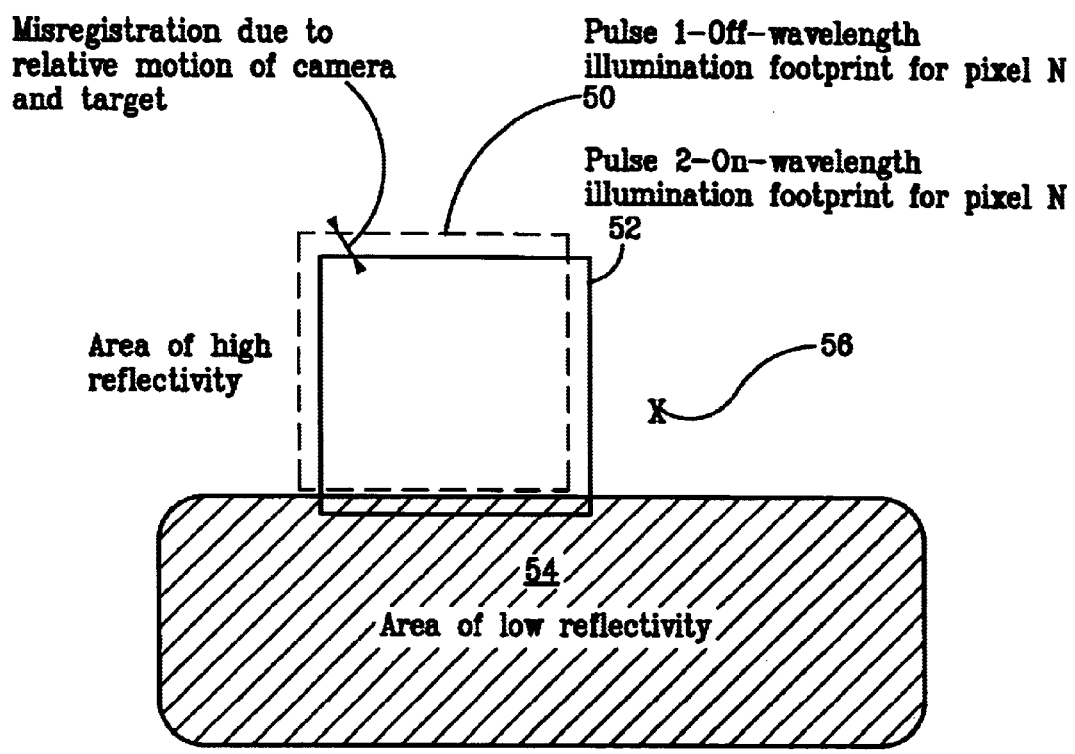
FIG. 5 depicts the spatial misregistration of on and off illumination of a pixel due to motion of the camera relative to the target.

The second condition depends on the tolerance that is allowed for signal errors caused by motion. The pulse sequence and temporal spacing are chosen so that biases due to system motion do not produce signals indicating the presence of gas when there is no gas in the FOV of a pixel. Given that the laser pulse is very short in duration, effects of motion result only from displacement of the camera or the target in the time between pulses. A bias occurs in a pixel when its FOV moves over a boundary between areas of different reflectivity in the time between the two laser pulses used to make the differential measurement. Referring to FIG. 5, the first wavelength 50 in the pair is chosen to be off the absorption of the gas, and the second wavelength 52 is chosen to be on the absorption. In all stationary measurements the pulse-energy-scaled backscatter for the on-wavelength should be less than that of the off-wavelength in the presence of gas. When motion occurs, it can cause the FOV of a pixel to move from a region of lower reflectivity 54 to higher 56 or vice-versa. The former cannot lead to a false alarm because it would result in an on-wavelength backscatter return having a higher value than an off-wavelength return and the processor can ignore data showing such an increase. The latter case can lead to a false alarm if the bias is larger than the threshold for detection. If a decrease in signal of X percent between off and on wavelength laser pulses in a given pixel is chosen to be the detection threshold, then motion of less than X percent of a pixel length will produce an apparent differential absorption of less than X percent under all reflectivity conditions. A design criterion of half of X percent pixel displacement between pulses is chosen to increase the immunity of the system to motion. As an example, for an embodiment that has a detection level of 10% absorption, motion of up to 5% of a pixel width would be allowed. This example is included in discussing the strategies below. In doing so, a field-of-view of 18 degrees and a resolution of 256×256 are assumed, so that each pixel subtends an angle of 1.2 milliradians. Five percent of this angle is 60 microradians. The allowable angular panning rate or the camera (i.e., the rate at which the camera can be swept over the scene) is given by $60 \times 10^{-6}$ radians divided by $t_{sep}$, where $t_{sep}$ is the time separation between laser pulses. This also gives a measure of the pointing stability required by the operator to achieve good handheld operation. For a vehicle-mounted application in which the imager is viewing orthogonally to the direction of motion, the maximum driving speed allowed, $v_{max}$, is given by $60 \times 10^{-6} * R / t_{sep}$, where R is the distance to the target being imaged. In all cases in which the example is used, a frame rate of 10 Hz is assumed.

Figure 6:
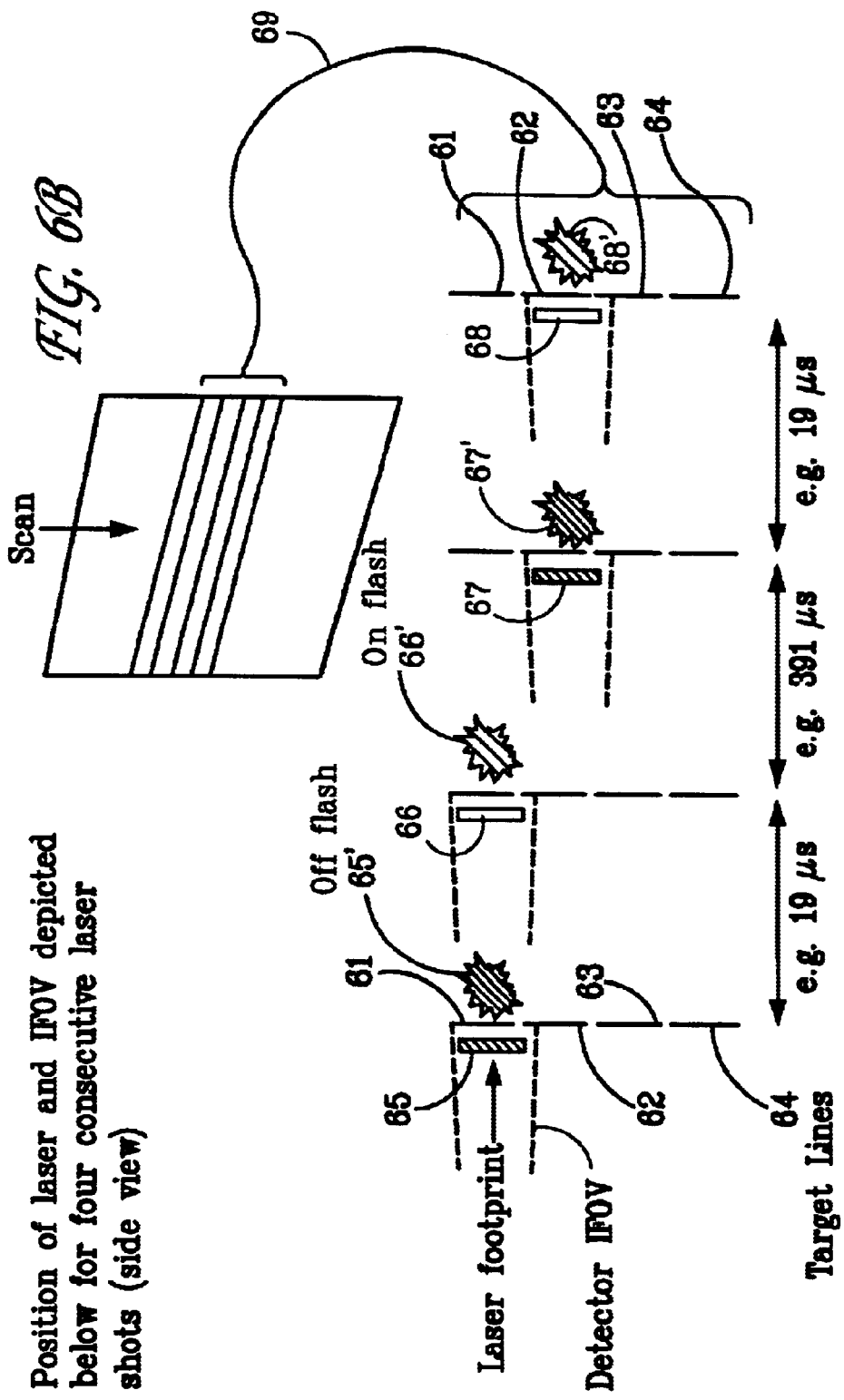
FIG. 6 depicts the scanning arrangement for Strategy 1 to minimize the effects of motion on differential imaging.

Seven strategies are provided for meeting conditions 2 and 3. The first strategy for meeting these two conditions is shown in FIG. 6 and uses a single scan mirror that sweeps smoothly in time to steer the laser beam and the IFOV of a linear array of detectors composed of 1×N elements, where N is the width of the array. Because only one row of pixels is used, requirement 3 is satisfied. The laser beam is uniformly formatted to illuminate the IFOV at the target. For single-wavelength imaging, the laser is pulsed at regular time intervals as the mirror aims it at each image line. For example, to meet the minimum acceptable frame rate of 10 Hz and assuming that the image is to be square (N×N pixels), a laser repetition rate of 10N pulses per second is required. Thus, if the image is to have a resolution of 256×256 pixels, a pulse repetition rate of 2560 Hz is needed. According to the example above for differential imaging, the laser must emit the on- and off-wavelength pulses during the time interval within which the laser pointing has moved ≦5% of the pixel width at the target. The detector array must be able to collect and store the backscatter signal from both wavelengths for a given line within this time interval. The laser pulses are generated by a single laser capable of emitting two pulses of different wavelength in a short time. For the example mentioned, the maximum time separation allowed is 5% of the time between on- and off-wavelength pairs of laser pulses or 5% of 1/(2560 Hz)=19 µs. With regard to the motion of the camera itself, this separation would allow a panning rate of 3.15 rad/sec (180 degrees/sec), or 10 camera FOV's/sec, assuming the example parameters described above. If imaging at a range of 20 m from a moving vehicle, this would allow a vehicle velocity of 136 miles/hr. FIG. 6A shows the position of the laser footprints and IFOV for four consecutive laser shots (side view). The same target lines 61–64 are depicted in each of the four shots, separated in time. Off wavelength laser footprint 65 producing off flash 65' is directed at target line 61. At a time interval not exceeding 19 µs, the on wavelength laser footprint 66, producing on flash 66', is directed onto line 61. At a time internal of less than 391 µs, laser footprint 67, producing off flash 67', is directed onto laser line 62. After a time duration of less than 19 µs, laser footprint 68, producing on flash 68', is directed onto target line 62. This cycle proceeds in the line-scanning direction for target lines 63 and 64 in the figure, and over an entire area to be illuminated in a scene under test. The time durations between laser pulses is this and the following strategies are exemplary only and other time durations can be used. FIG. 6B shows target lines 61–64 over an area 69 under test.

Figure 7:
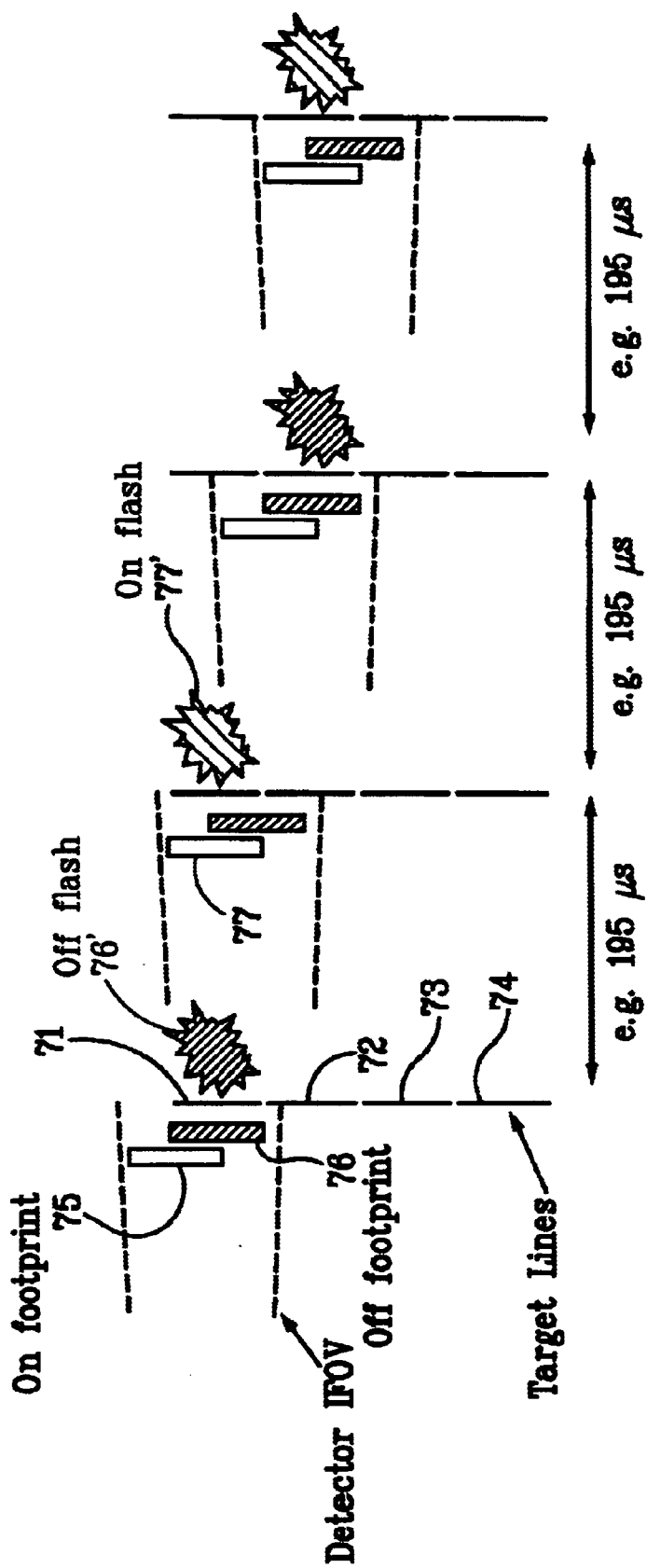
FIG. 7 depicts the scanning arrangement for Strategy 2 to minimize the effects of motion on differential imaging.

The second strategy for meeting conditions 2 and 3 also uses a continuously-swept scan mirror. It achieves registration by adjusting the launch angle of the laser beam from the scan mirror so that the pulses illuminate the same target spot even though they are separated in time (FIG. 7). This allows a longer time separation between laser pulses than the first strategy. The detector IFOV is designed to view a region at the target that is at least 1.5 times as tall (in the scan direction—in the description of this strategy, the scan direction is referred to as the vertical direction) as the laser illumination. This can be accomplished, for example, by selecting the appropriate anamorphic optics to make the IFOV of each pixel at least 1.5 times as tall as it is wide. It can also be accomplished by using a 2×N array to view the scene and reading both lines for each laser shot and adding the output of each pair of pixels in a given column to generate the signal for a particular laser shot. If it uses one row of detectors it will meet condition 2; if it uses two rows of detectors it will not meet condition 3 and will require nonuniformity correction. In all cases, the laser illuminates only a region having a vertical angular extent that is ≦2/3 that of the IFOV. Because essentially all the light used to make the image comes from laser backscatter, the vertical extent of the laser determines the vertical resolution of the line. The laser is adjusted to fire the on- and off-wavelength pulses with a relative vertical angular separation equal to the angular spread of the laser sheet in that direction. This can be achieved passively, by using two lasers each pointing in a slightly different direction or by using a diffractive element that steers each wavelength in a slightly different direction, or it can be achieved actively by using a mechanical or electro-optical element to dither the beam up and down synchronously with the pulsing of each wavelength. Assuming the conditions of the above example, the laser repetition rate would have to be 2×2560=5120 Hz. This would allow a time separation between pulses of 195 μs, leading to a panning rate of 0.3 rad/s (18 degrees/s), or 1 camera FOV/s. If imaging at a range of 20 m from a moving vehicle, this would allow a vehicle velocity of 13.3 miles/hr. FIG. 7 thus shows how angular dithering changes location of on and off footprints. The same set target lines 71–74 are shown in four consecutive laser shots, each set separated in time by 195 μs in the figure. Notice that the positional location of the on-footprint 75 overlaps about half of the off-footprint 76 producing a combined footprint about 1.5 times the coverage of a single footprint and requiring a detector IFOV at least 1.5 footprint diameters. In the figure, off-footprint 76, producing off flash 76', is directed onto target line 71. At a delay of 195 μs, on-footprint 77, producing on-flash 77' is directed onto target line 71. This sequence continues in the scan direction over a scene under test.

Figure 8:
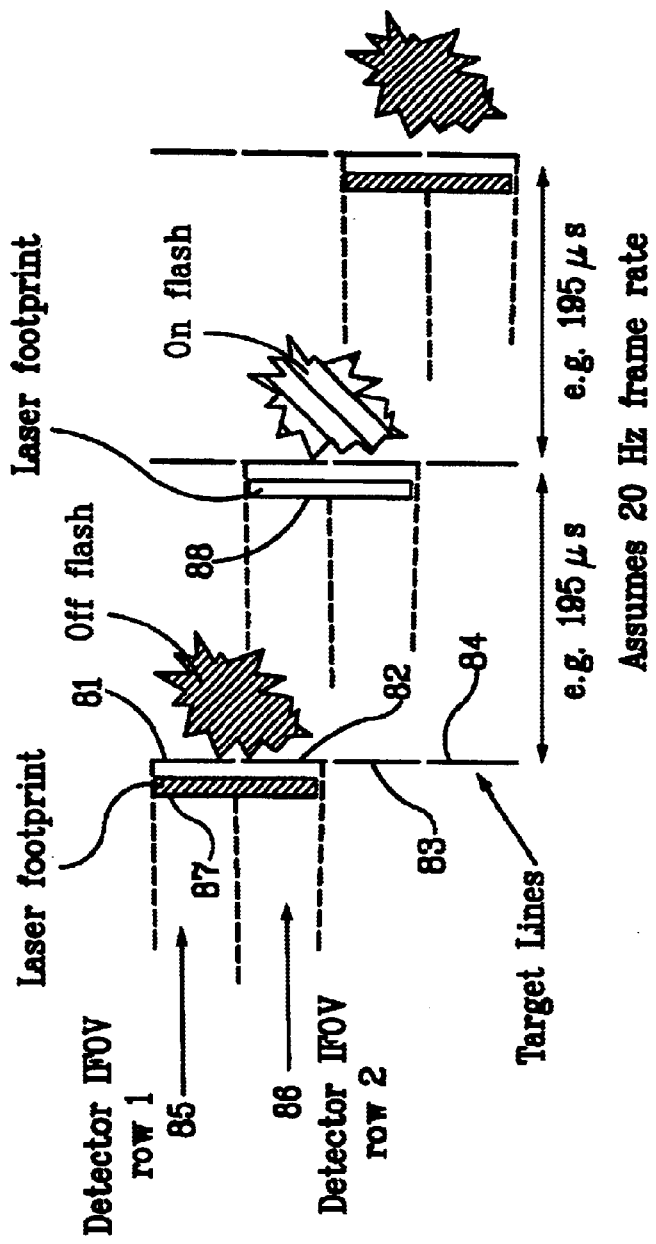
FIG. 8 depicts the scanning arrangement for Strategy 3 to minimize the effects of motion on differential imaging.

FIG. 8 illustrates a third strategy for meeting conditions 2 and 3 that also uses a continuously-swept scan mirror. Unlike the second strategy, it does not adjust the angle of the on- and off-wavelength beams. Instead, it achieves registration by illuminating two rows of target pixels (target lines) simultaneously with a laser sheet that is sized to overlap a 2×N area on the target, where N is the vertical (scan) direction, as before. The illuminated area is viewed by a 2×N detector array. Because a different row of detectors is used for each wavelength, condition 3 is not met and nonuniformity correction is required. As can be seen in FIG. 8, the illumination and viewing regions are stepped down one row between laser shots. Each laser shot produces a target interrogation of two lines at a given wavelength. As can be seen in the figure, by stepping down in one line steps, the entire target area is ultimately viewed under illumination by both wavelengths. According to the parameters of the example, the laser repetition rate can be 1280 Hz for single-wavelength imaging and 2560 Hz for differential detection. The lower repetition rate results from the fact that two rows are illuminated each shot. Alternatively, the frame rate can be increased to 20 Hz, requiring a laser repetition rate of 5120 Hz as in strategy 2. This would allow a time separation between pulses of 195 μs, leading to the same panning and driving rate limits as for strategy 2. In the figure, the set of target lines 81–84 are shown separated in 195 μs time intervals. A first detector IFOV row 85 is adjacent to a second detector IFOV row 86. The off-laser footprint 87 covers both target lines 81 and 82. The laser is scanned such that the on-footprint 88 covers both target lines 82 and 83. The sequence continues over a scene under test. It is possible to extend this approach to illumination of more than two rows in conjunction with an array having more rows.

Figure 9:
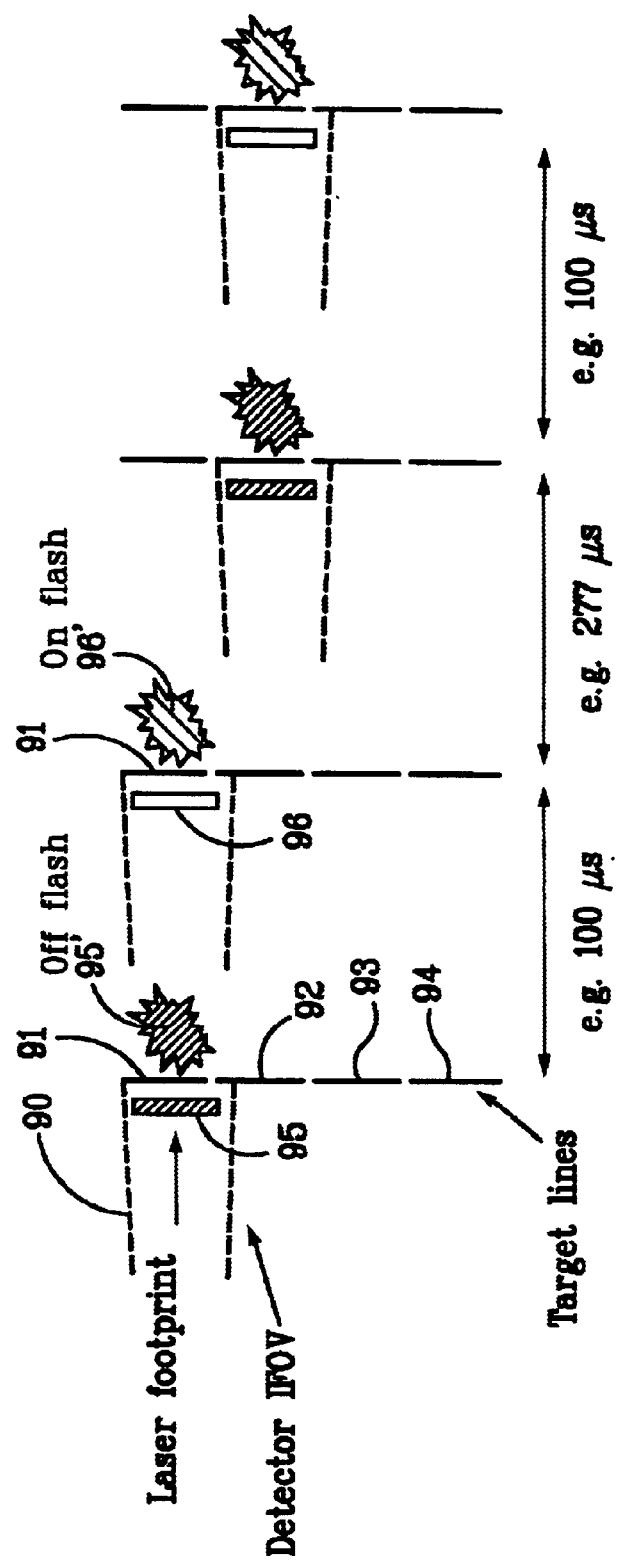
FIG. 9 depicts the scanning arrangement for Strategy 4 to minimize the effects of motion on differential imaging.

FIG. 9 shows a fourth strategy for meeting conditions 2 and 3 that uses a mechanical scan mirror that is step-scanned instead of smoothly-scanned. The mirror is stepped to view each line and stopped. During the time in which it is stationary, the two laser pulses are fired, spaced in time, and the backscattter signal is collected after each pulse is fired. It is then stepped to view the next line and the process is repeated. The target is viewed using a 1×N detector array, meeting condition 3. Stepping continues until the full frame is collected. The maximum step time allowed between shots for the example cited above is 1/(2560 Hz)=377 μsec. Assuming that the mirror is stationary for 100 μsec of this time and that 277 μsec is reserved for stepping time, the panning rate allowed by this separation is 0.6 rad/s (34 degrees/s), or 1.9 camera FOV's/s. The vehicle motion allowed is 26 miles/hr. In the figure, the set of target lines 91–94 are shown spaced apart in time. Off-Laser footprint 95, within the detector IFOV 90, is directed onto target line 91, producing off-flash 95'. After a delay of 100 μs, the on-laser footprint 96, within IFOV 90, is directed onto target line 91, producing on-flash 96'. The laser footprints and the detector IFOV are scanned to the next target line and the process is repeated after a delay of 277 μs.

Figure 10:
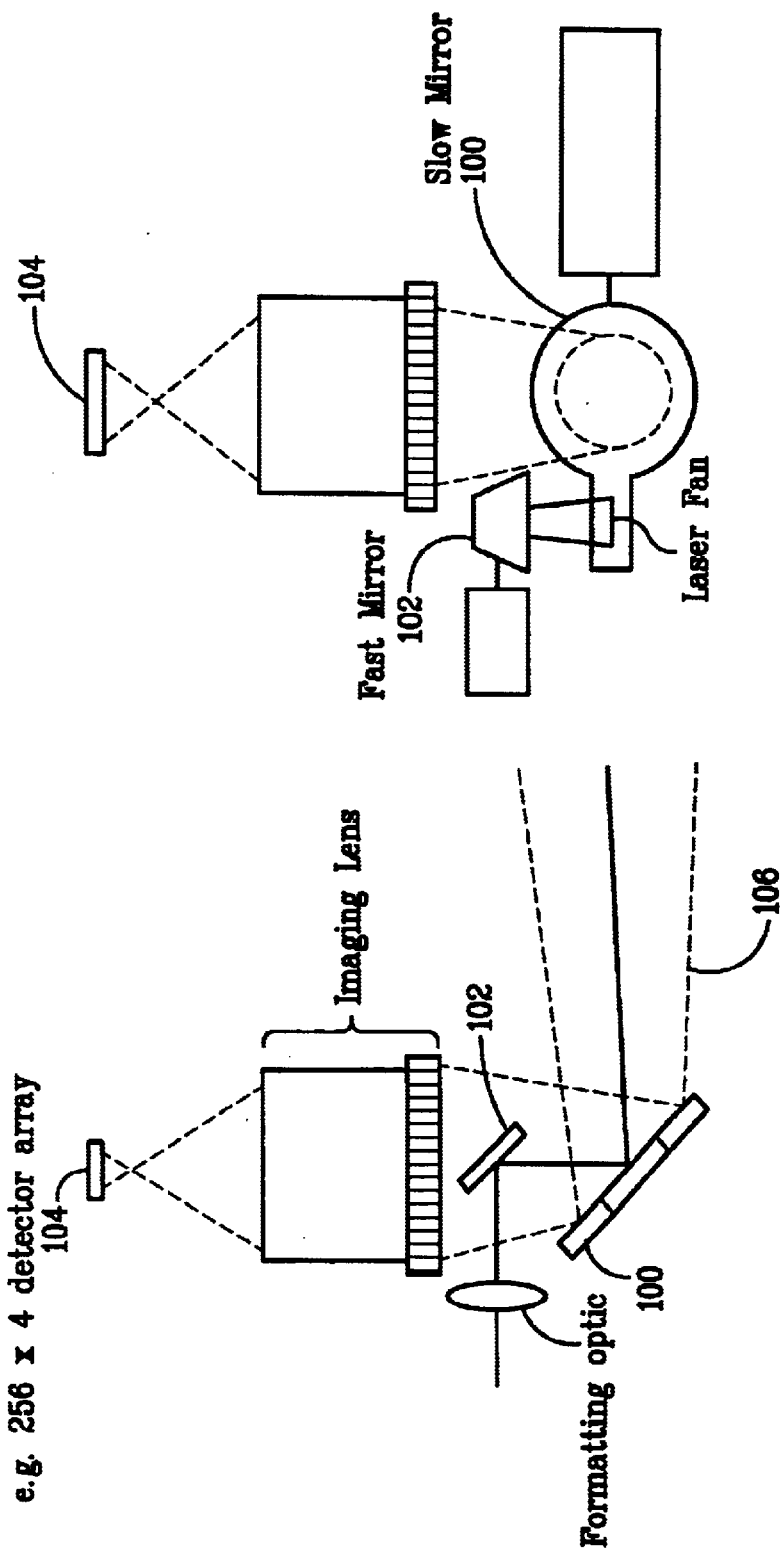
FIG. 10 depicts the optical arrangement for Strategy 5 to minimize the effects of motion on differential imaging.

An optical set-up for accomplishing a fifth strategy for meeting conditions 2 and 3 is shown in the side view of FIG. 10A and the front view of FIG. 10B. This strategy relaxes the need for a fast stepped mirror by using two stepped mirrors 100, 102 and a detector array 104 with a dimension of more than one pixel in the vertical direction (i.e., a format of M×N elements, where M is the number of vertical elements). This is advantageous in cases where the size of the scan mirror required is too large to allow it to be stepped in a short enough time for real-time imaging. In this approach, each target line uses the same detector row for both wavelengths, thus meeting condition 3. The two scan mirrors are referred to as the slow mirror and the fast mirror. Referring to the figures, the fast mirror 102 reflects only the laser and can, thus, be made small. It directs the laser beam to the slow mirror 100, which reflects both the laser and the IFOV 106 to the target. Because the slow mirror 100 does not require fast steps, it can be made larger than in the single-stepped-mirror case.

Figure 11:
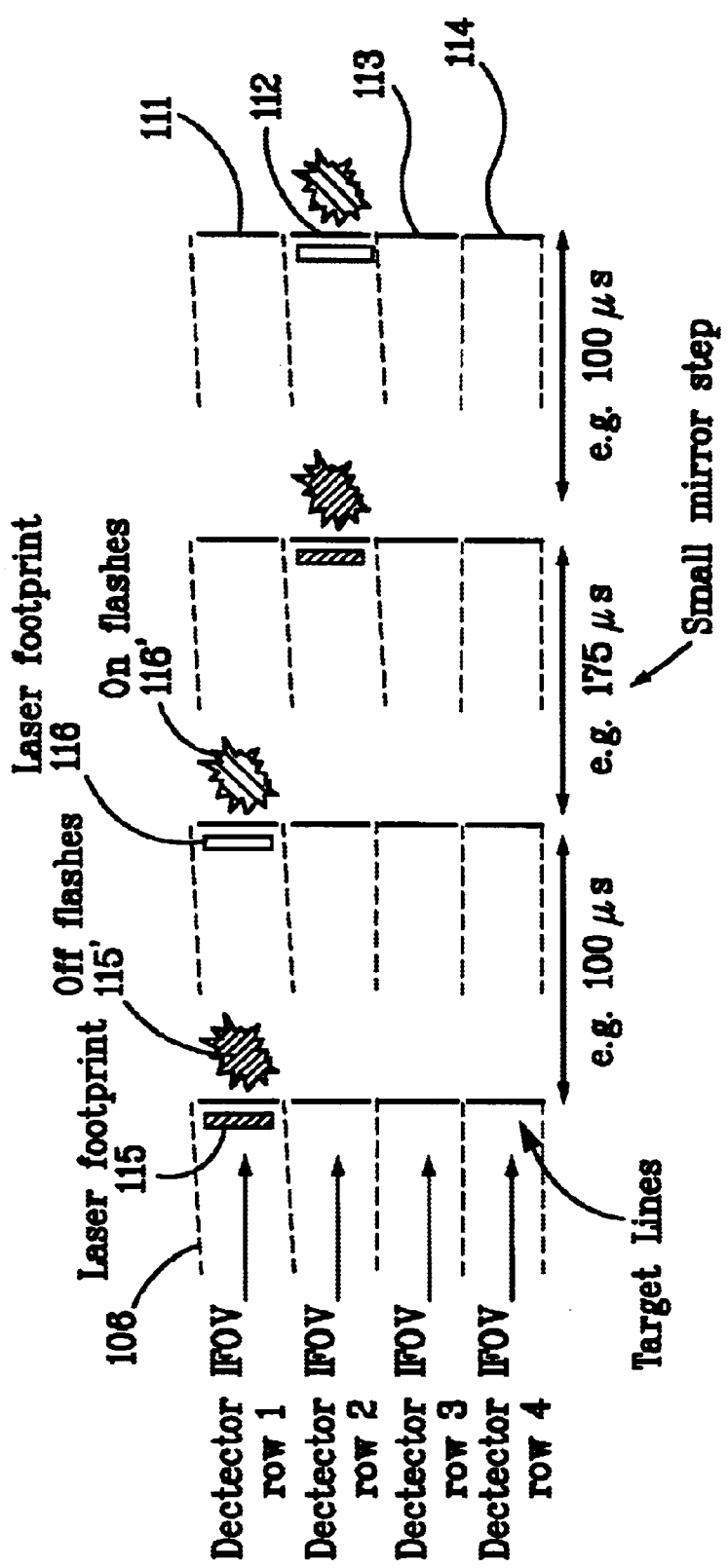
FIG. 11 depicts the scanning arrangement for Strategy 5 to minimize the effects of motion on differential imaging.

Referring to FIG. 11, at the target, the IFOV 106 views M lines (shown as target lines 111–114 in the figure) at any position of the slow mirror. While the slow mirror is stationary, the fast mirror can step the laser illumination across these M lines. At each step point of the fast mirror, the laser is fired once for single-wavelength imaging or twice for differential imaging. After each firing, the M×N array is read out and the relevant line of information is extracted from it. If an array is available that can read out one selected line, then only the relevant line is read. After the M lines are illuminated and read, the slow mirror moves to aim the IFOV to the next M lines and the process is repeated. This continues until the full image is collected. Consider again the example of a 256×256 image collected at 10 Hz. If a 256×4 array is used, the slow mirror moves in four-line jumps. If it is assumed that the on- and off-wavelength pulses are fired within 100 μs and the fast mirror requires 175 μs to step, the slow mirror is allowed 635 μs to step. This is almost a factor of two slower than in the single step-mirror case. The 100 μs separation leads to the same panning rates and vehicle velocities described in the third strategy. In the figure, the detector IFOV 106 views target lines 111–114 simultaneously. Off-laser footprint 115 is directed onto target line 111, producing off-flash 115'. After a time delay, e.g., 100 μs, the on-laser footprint 116 is directed onto target line 112, producing on-laser flash 116'. After a delay, e.g., 175 μs, the fast mirror 102 is then advanced to the next target line 112, and the process is repeated.

Figure 12:
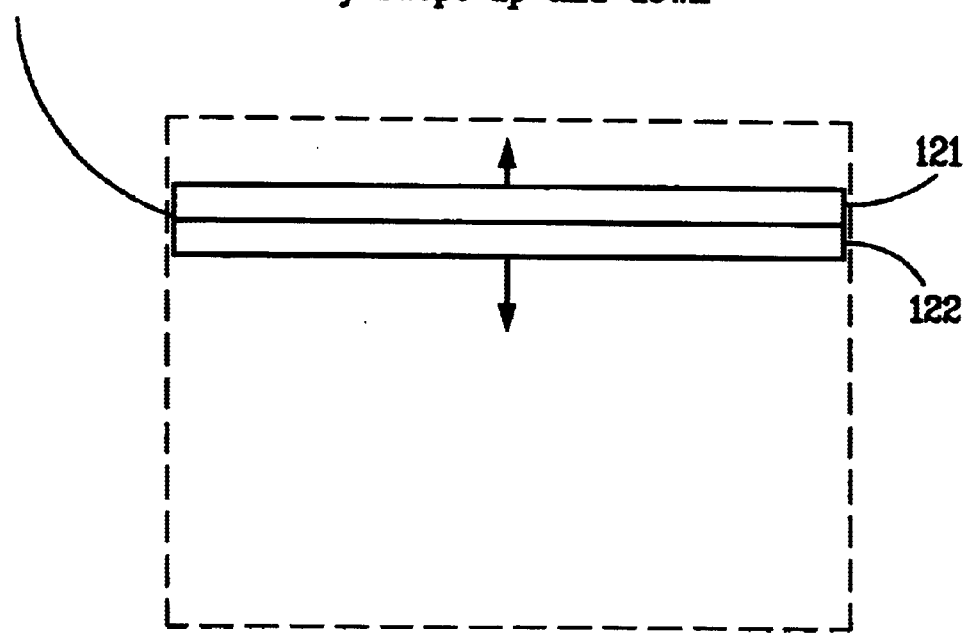
FIG. 12 shows the two-dimensional focal plane array capable of electronically-swept windowing used for Strategy 6 to minimize the effects of motion on differential imaging.

Referring to FIG. 12, the sixth strategy for meeting conditions 2 and 3 uses a two-dimensional array whose vertical dimension matches the number of lines (e.g., lines 121 and 122), to be imaged. The array is operated in a windowed mode in which only a small segment of the array (e.g., 1×N, 2×N, etc) is used to image the backscatter return from a particular laser pulse. The location of this window on the 2-d array is set electronically and can be shifted from one pulse to the next. This strategy can be used to eliminate the need for a scan mirror to steer the detector IFOV. It could be used with all of the above formats, replacing the need to scan the IFOV with a scanning mirror by the use of electronic scanning. Depending upon how it is used, this approach may or may not satisfy condition 3 and may or may not require nonuniformity correction. The panning and driving rate allowed would be dependent upon the mode in which it is implemented, as described above.

Figure 13:
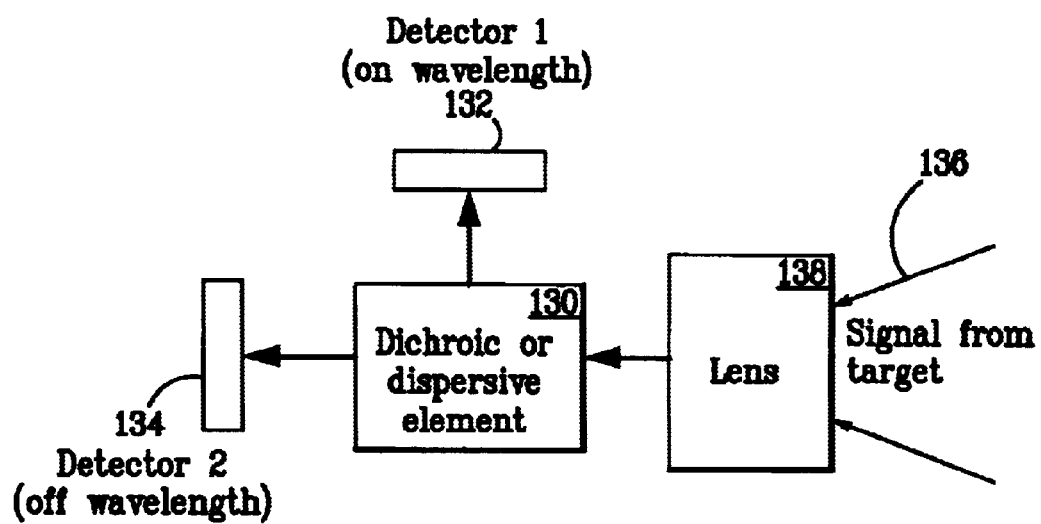
FIG. 13 shows the optical layout used to spectrally separate the on- and off-wavelength return signals onto two separate detectors (or two regions of the same detector) to satisfy the requirements of Strategy 7 to minimize the effects of motion on differential imaging.

The seventh (FIG. 13) strategy employs two transmitter lasers, one at a wavelength on the absorption and one at a wavelength not absorbed by the gas. It uses dispersive or dichroic elements 130 in the receive optics and two focal plane arrays 132, 134 (or two regions on the same focal plane array) for simultaneous measurement of the backscattered radiation at the two wavelengths. Signal 136 from the target is collected by lens 138. Dichroic or dispersive element 130 directs light from the on-wavelength to detector 132, and directs light from the off-wavelength to detector 134. It is consistent with an approach that would use a smoothly sweeping scan mirror or a step-scanned mirror, where the mirror sweeps the field-of-view of each array simultaneously. The mirror could be replaced by an electro-optic or acousto-optic deflector as well. It could also be implemented using arrays that are capable of rolling windowed operation, as in strategy five above. Because there would be zero difference in time between the on- and off-wavelength laser pulses, there would be no restriction on movement as it affects on- and off-wavelength pixel registration. It would, however, be subject to movement restrictions related to image smearing (i.e. frame rates ≧10 Hz necessary for smearing avoidance under ordinary circumstances.

Requirement 5, above, for a uniform illumination is met by using a beam homogenizer/transmitter. This device must produce a reasonably uniform line of illumination at the target with a horizontal angular spread dictated by the desired angular FOV and a vertical spread that is consistent with the selected illumination strategy. The homogenizer converts the beam from a near Gaussian intensity profile to a uniform profile. The transmitter projects the uniform irradiance onto the target in the form of a line that is matched to the horizontal and vertical field-of-view of the focal plane array (FPA).

Figure 14A:
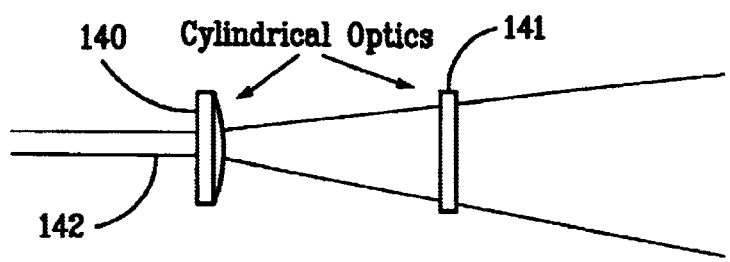
FIGS. 14A–D are diagrams of the four illuminator concepts using cylindrical optics (14A); cylindrical optics plus a mixing rod (14B); cylindrical optics plus a multifaceted optic (14C); patterned quasi-phasematched crystal (14D).

Four methods of constructing this subsystem are depicted in FIGS. 14A–D. FIG. 14A shows a pair of anamorphic cylindrical projection lenses 140, 141 that will spread the laser beam 142 as a line onto the target. Homogenization will be achieved by using only the central portion of the line, which will have a Gaussian intensity distribution across its length. If this method is used, some laser power will be sacrificed at the edges of the line and the illumination will still have some curvature.

Figure 14B:
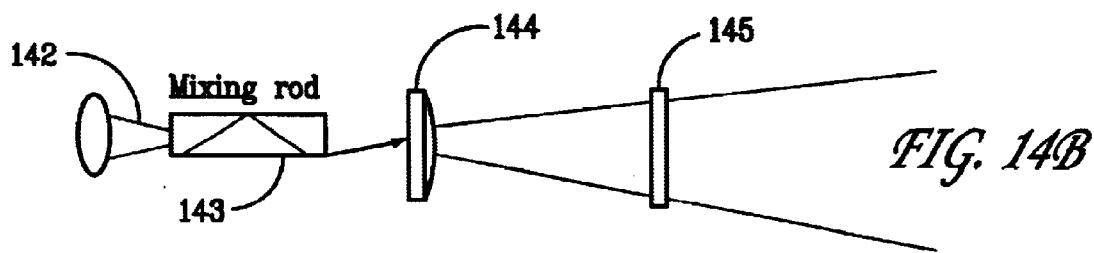

The second method, shown in FIG. 14B, involves the use of a mixing rod 143 to homogenize the beam 142 into a uniform rectangular illumination, present at the exit face of the rod. The exit face is then projected onto the target with the appropriate anamorphic magnification by a pair of cylindrical optics 144, 145. This method is favorable over the first because it produces an inherently uniform illumination.

Figure 14C:
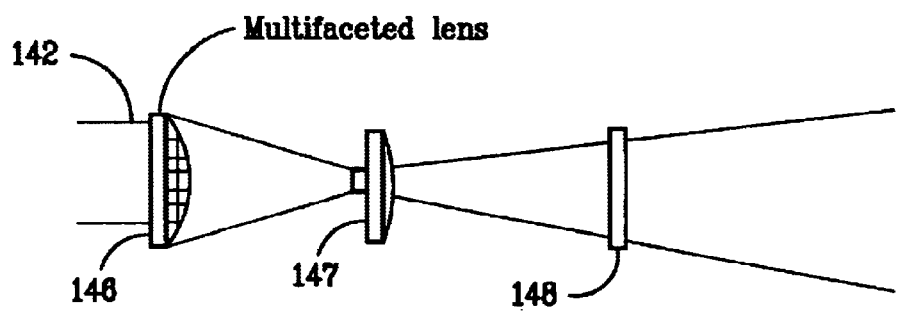

The third method, shown in FIG. 14C, uses a multifaceted projection optic 146 to homogenize the beam 142 (in a similar manner to the mixing rod 143) and project it as a uniform rectangle in space. This rectangle would then be imaged onto the target by cylindrical optics 147, 148. The multifaceted optic 146 can be a lens with faceted elements on one side that serve as a prism array. Alternatively, suitable prism or cylindrical lens arrays serve a similar purpose.

Figure 14D:
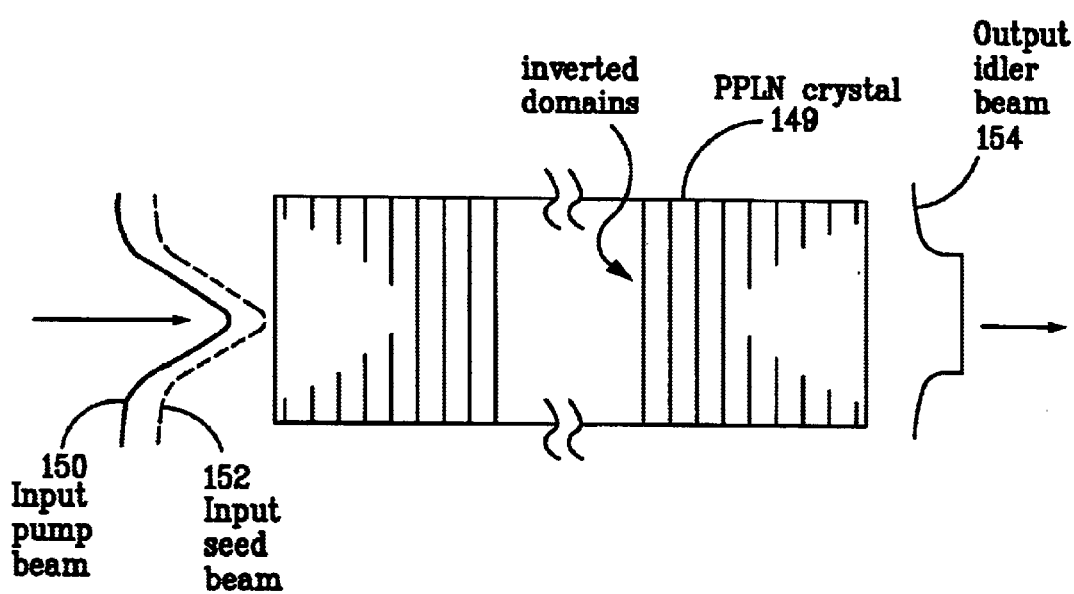

The fourth method, shown in FIG. 14D, uses a quasi-phasematched nonlinear crystal 149 whose region of periodicity is spatially patterned (as in "Lateral Patterning Of Nonlinear Frequency Conversion With Transversely Varying Quasi-Phase-Matching Gratings" by Imashev et al. Optics Letters 23 673–675 (1998)) to produce a flattop output from a Gaussian input when a nonlinear mixing process is performed. The process performed in this case could be either parametric amplification or parametric generation where a pump beam is converted to signal and idler beams whose frequencies add to that of the pump beam. The lateral patterning of the QPM crystal would cause the signal or idler beam to be formed with a flattop shape. This shape could then be spread onto the target using anamorphic optics as in the first method mentioned above. This would eliminate the sacrifice of laser power and curvature of the illumination intensity. The figure shows an input pump beam 150 and an input seed beam 152, where both beams have a Gaussian shape and are input to the crystal 149 (e.g., PPLN) which produces an output signal or idler beam 154 that has a flat top shape.

Detailed Description of Specific Embodiment

Specifications and Calculations

Figure 15:
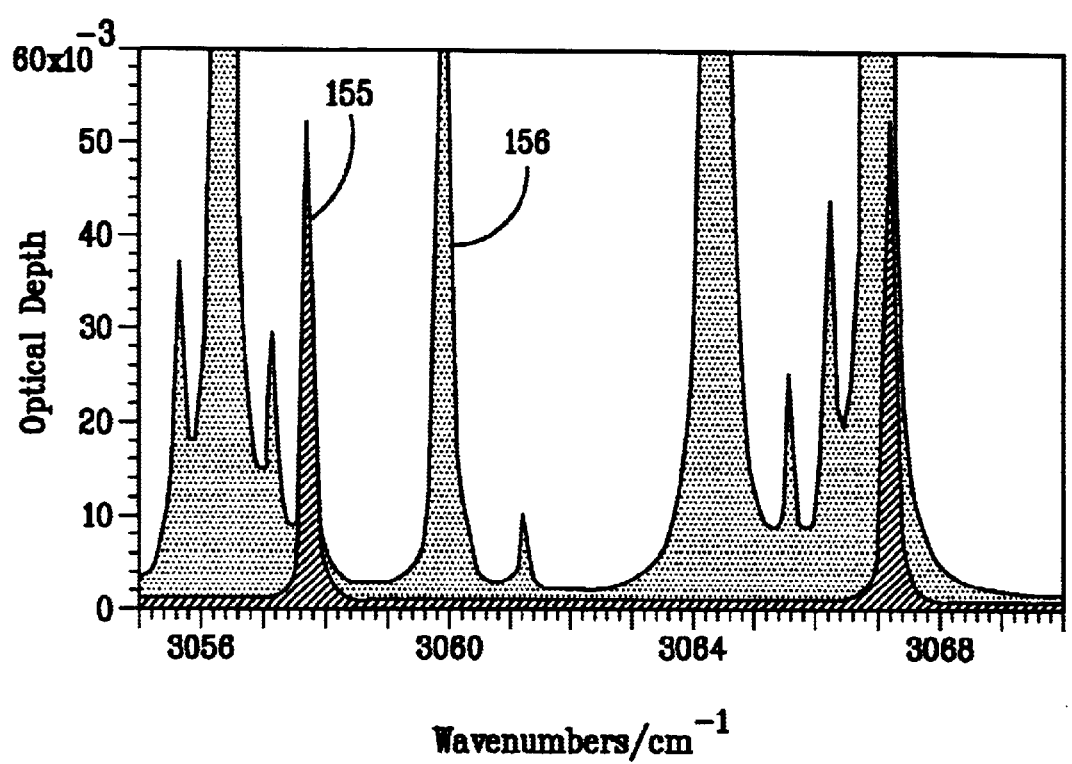
FIG. 15 is a plot of the optical depth of methane at a density of 10 ppm-m and water vapor at a density of 0.038 atm-m. The dark features are methane and the light features are water vapor plus methane.

This section describes a specific embodiment of the differential BAGI device of the present invention. For this design, the following specifications are assumed:

1. Gas to be detected—methane;
2. Wavelength for detection—mid-IR (~3 μm);
3. Detection sensitivity—10 ppm-m;
4. Maximum standoff range—5 m;
5. Frame rate—10 Hz;
6. Field-of-view—18×14 degrees;
7. Resolution—262×220 pixels A strong methane absorption band in the mid-IR is the $\upsilon_3$ rovibronic band centered at ~3018 $cm^{-1}$. This band was analyzed to determine a suitable operating wavelength for the handheld imager, which was found to be 3057.7 $cm^{-1}$. FIG. 15 contains a plot of the portion of the $\upsilon_3$ band containing this feature, calculated for a single pass through a methane plume density of 10 ppm-m. The calculation also assumed the presence of the only significant interferent (water vapor) present at a density of 0.038 atm-m. The features with reference number 155 are methane and the features with reference number 156 are water vapor plus methane. It is evident that this concentration of methane will produce a roundtrip optical depth of 0.11 and will not overlap significantly with water vapor at this high humidity.

Additional inspection of the spectrum in FIG. 15 indicates that the laser must be centered within +/−1.5 GHz of the peak of the absorption (to produce an optical depth within 10% of the peak value). For optimal differential detection, the off-wavelength should be positioned in the valley at the high-wavenumber side of the methane absorption. For optimization of the differential detection within the valley, the off-wavelength should be at least 8 GHz away from the on-wavelength line and positioned at an accuracy of +20/−0 GHz to remain in the valley.

Figure 16:
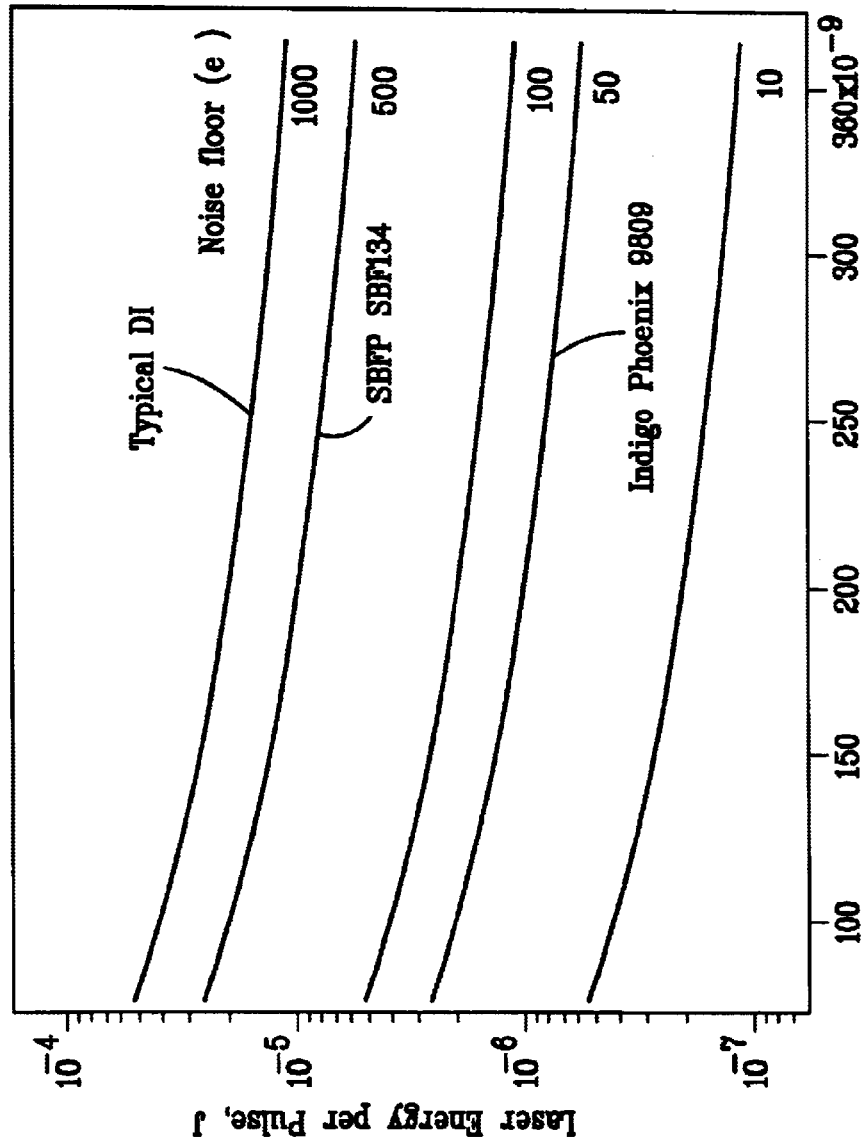
FIG. 16 is a plot of the laser energy per pulse required to achieve the minimum signal-to-noise ratio according to Equation 5.

For the handheld imager, sensitivity will be calculated assuming differential detection. As indicated above, a roundtrip absorption by 10 ppm-m of methane will cause an optical depth of 0.11. It is assumed that a plume of this density must be detected at a signal-to-noise ratio of 5 (i.e., the change in return signal must be greater than or equal to 5 times the noise level). This sets the required signal-to-noise ratio of the single-wavelength backscatter signal to $5 \cdot \sqrt{2}/0.11=64$ where the factor of $2^{1/2}$ is included because the error of two ratioed pixels (the on-wavelength and the off-wavelength) are combined to generate the differential signal. It is assumed that the reflectivity is the same for both wavelengths. Thus, to produce the required sensitivity it is necessary to generate a backscatter signal-to-noise ratio of 64 in both the on-wavelength and off-wavelength returns. The calculations are made assuming that residual speckle noise following differential detection is negligible compared to the systematic noise. Speckle is the result of using a coherent (i.e. laser) light source, and it is highly dependent on the actual scattering surface and viewing geometry. The inherent signal-to-noise ratio of the imager should be low enough that when systematic noise is dominant, adequate sensitivity is achieved for the detection application. The measurement will be made at sufficiently small time and frequency separation between the on- and off-wavelength measurements that the speckle will be correlated and should ratio out. The laser pulse energy and receiver attributes can be calculated using the required backscatter return signal-to-noise ratio and a standard lidar equation. The required energy per pulse depends on the transmitter and receiver efficiencies, the atmospheric transmission coefficient ($m^{-1}$), the target range (m), the target reflectivity, the detector noise-equivalent energy (J), the number of elements in the linescanner linear array, the width of those elements (m), the collection f/#, and the system field-of-view (degrees). Results of calculations using typical values are shown in FIG. 16. Each curve corresponds to a different detector noise floor. The energy required for some available focal-plane arrays (FPAs) is indicated, assuming that a linear region of 262 horizontal pixels is used. A noise floor of 50 electrons is obtainable at the present commercial state-of-the-art. Thus, it can be concluded that a minimum laser energy per pulse of about 1 $\mu$J is required to meet the signal-to-noise performance at a range of 5 m.

The sections below describe particular embodiments of the laser, camera, and image frame assembly and processing system. In this specific embodiment for the system the illumination strategy of FIG. 9 is assumed.

Light Source

The narrowband light source consists of a pump laser and a frequency conversion device. Specifications for the light source are listed as follows:

1. Emits≧1 $\mu$J per pulse
2. Emits at on-wavelength of 3057.7 $cm^{-1}$, locked to a precision of +/−1.5 GHz;
3. Emits at off-wavelength of between 3057.8 and 3058.4 $cm^{-1}$;
4. Repetition rate and wavelength switching for selected illumination strategy The requirement for a pulsed tunable narrowband light-source leads us to a frequency-conversion device driven by a pump laser. These two components, the (1) frequency converter and (2) pump laser, are discussed below. The efficiency of the frequency conversion device will define the required power of the pump laser, assumed to emit 1.064-$\mu$m radiation.

Frequency Conversion Device

Figure 17:
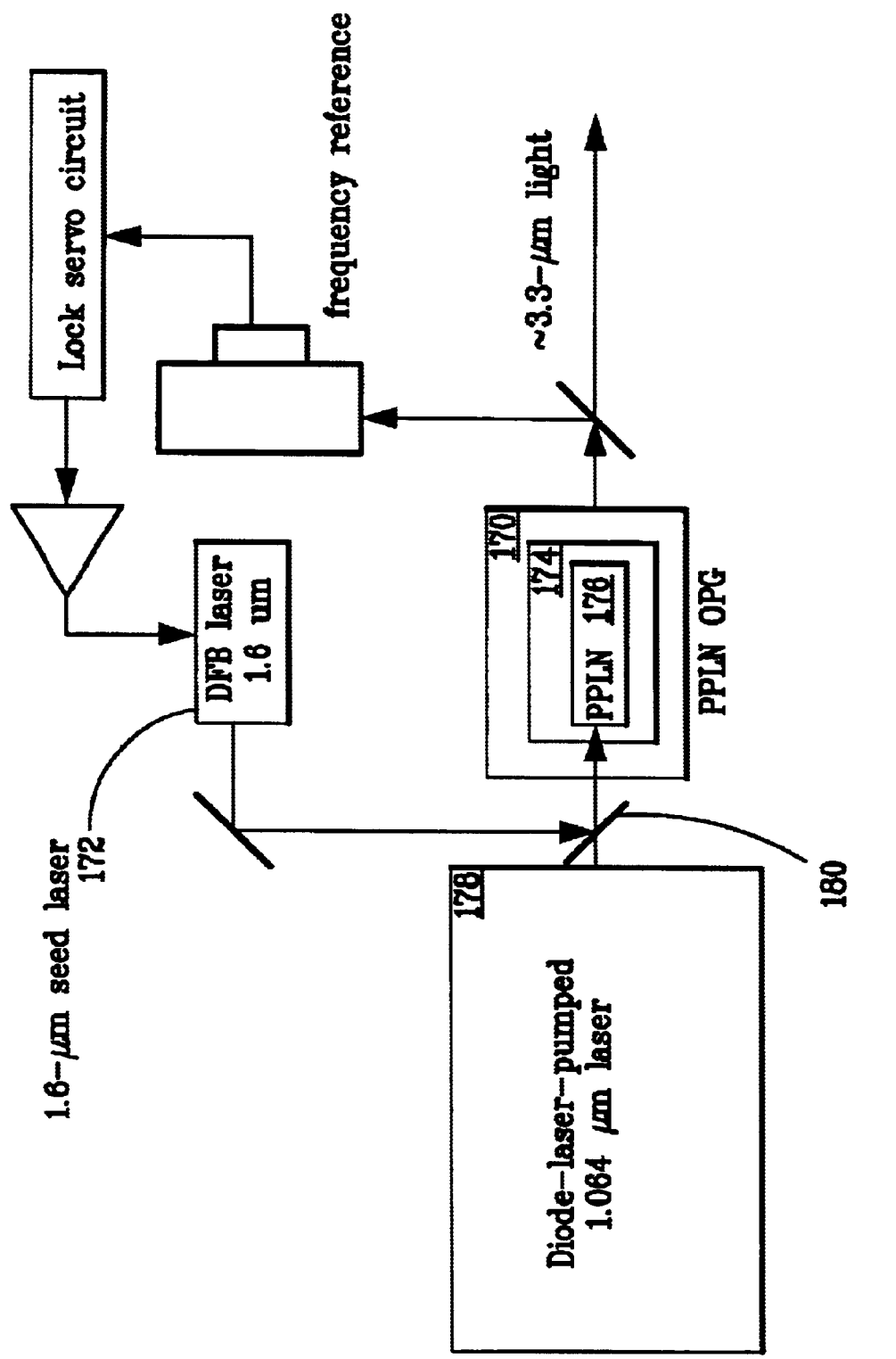
FIG. 17 is a diagram of a laser system for the handheld imager.

The device selected in this embodiment to produce pulsed radiation at the target methane transition (3057.7 $cm^{-1}$) is a parametric frequency converter pumped by a 1.064 $\mu$m laser. This device converts a pump beam photon at 1.064 $\mu$m into photons at the signal (~1.6 $\mu$m) and idler (~3.3 $\mu$m) wavelengths, where $\nu_{pump}=\nu_{signal}+\nu_{idler}$. In the embodiment of the frequency conversion device, an optical parametric generator (OPG) performs the frequency conversion. A diagram of a laser-pumped OPG 170 suitable for a handheld gas imager is provided in FIG. 17. It is seeded by a fiber-coupled distributed feed back (DFB) laser 172 housed in a standard semiconductor package. The package contains the thermoelectric temperature controller 174 and an optical isolator. The PPLN crystal 176 is 2–5 cm in length, 0.5–1 mm thick, and as narrow as permissible while maintaining structural integrity (3–4 mm). It is housed in a TE-heated oven to regulate its temperature. MgO-doped PPLN may be used to minimize the heating requirements. The pump beam from a diode-pumped 1.064 $\mu$m laser 178 and the collimated fiber-output of the DFB laser are coupled into the PPLN via a simple optical coupler 180.

For control of the on-off frequency dither, the DFB laser current is varied to produce a wavelength change between the on-resonance and off-resonance wavelengths at half the laser repetition rate. A smaller dither leads to less speckle decorrelation, a source of noise in the In-ratio differential absorption measurement. In addition to the seed and the wavelength-conversion device, a feedback-control system may be required to stabilize the output wavelength to the methane line, and this control may be incorporated into the electronics that control the dithering of the laser wavelength.

Pump Laser

Figure 18:
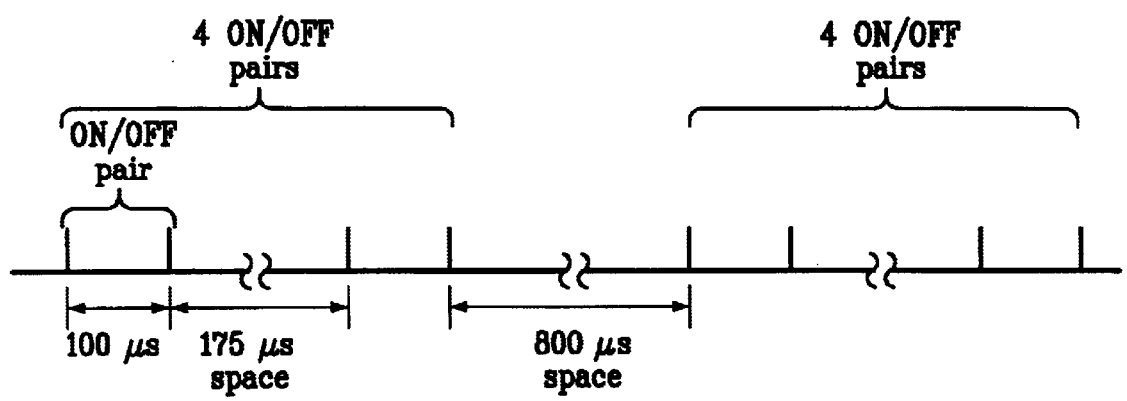
FIG. 18 shows a pulse timing scheme for acquiring the differential image.

The laser requirements are dictated by the image-acquisition scenario described in FIG. 18. The pulse timing sequence, shown in FIG. 18, requires b 100$\mu$sec between the on- and off-wavelength pulses and ~175 $\mu$sec between the on- and off-wavelength pulse pairs. After four pairs, there will be a ~800 $\mu$sec delay before this cycle begins again.

The major design constraints for the 1064-nm pump laser design are the 100-$\mu$sec delay between the on-methane and off-methane pulses (see FIG. 18) and the output energy greater than 1 $\mu$J/pulse. These requirements, together with the overall efficiency of the laser designs, determine the total pump power required from the diode laser(s). For Nd:YAG, the 100 $\mu$sec pump interval is considerably shorter than the fluorescence lifetime of 230 $\mu$sec, resulting in a favorable value of the storage efficiency (low loss to spontaneous emission). Nd:YVO$_4$, which has a fluorescence lifetime of ~100 μsec, is a potentially more attractive laser material for the timing requirements of the pump laser.

Camera

Example specifications for the infrared camber are listed below. The term camera is used to describe the portion of the imager containing the infrared detector array, readout circuitry, analog-to-digital converters for the image data, and electronics to output the data to the image processing and display.

1. Low read noise floor (~50 electrons);
2. Capable of snapshot gating with a short gate width (~1 μs);
3. Capable of efficiently integrating short laser pulses;
4. Readout rate consistent with illumination strategies;
5. Contained in a dewar with ~f/1 coldstop;
6. Linear array desirable; 2-d array with windowing acceptable; and
7. Produce line output data in a digital format.

This embodiment of the pulsed laser linescanned imager uses an infrared camera that contains a focal plane array (FPA). The focal plane array is a hybridized InSb photodiode array with a charge transimpedence amplifier readout circuit. Other embodiments could use Mercury Cadmium Telluride (MCT) detectors and different types of readout circuitry. Hybridized InSb and MCT FPA's consist of a diode array that is bump-bonded to an array of silicon readout circuits. Several types of readout circuits are used in FPAs including (1) direct injection (DI), (2) buffered-DI, and (3) charge transimpedence amplifiers (CTIA). The temporal response of the array to short laser pulses is dependent upon the type of readout used. The response is characterized by instantaneous integration of the charge on the diode junction, followed by a slower readout of the charge to an integration capacitor located in the readout unit cell. The detector junction can saturate if the amount of charge placed in the detector is enough to de-bias the junction. Thus, the detector should be selected to operate with a junction capacity that equals the expected maximum signal. Of the three types listed above, readouts based on DI circuits are the most widely available devices; however, they exhibit the slowest readout times (~200 μs). The CTIA readout has a transfer time of 1–2 μs. The buffered-DI is also relatively fast (estimate 10's of μs), but can exhibit some nonlinearity.

Frame Assembly and Processing

The frame assembly and processing system (FAPS) accepts digital data from the camera, performs the necessary processing, and outputs real-time video. A specific embodiment of the FAPS could use a single-board computer (SBC) with a frame grabber card to perform these functions. The frame grabber is used to receive the data from the camera and buffer it so that the data can be read asynchronously by the computer. A program running in real-time on the computer can take the data from the frame grabber, extract the laser-illuminated pixel rows from the 4-row camera frames, perform the differential imaging computations (if in differential mode), assemble complete images, and send the images to the display.

Figure 19:
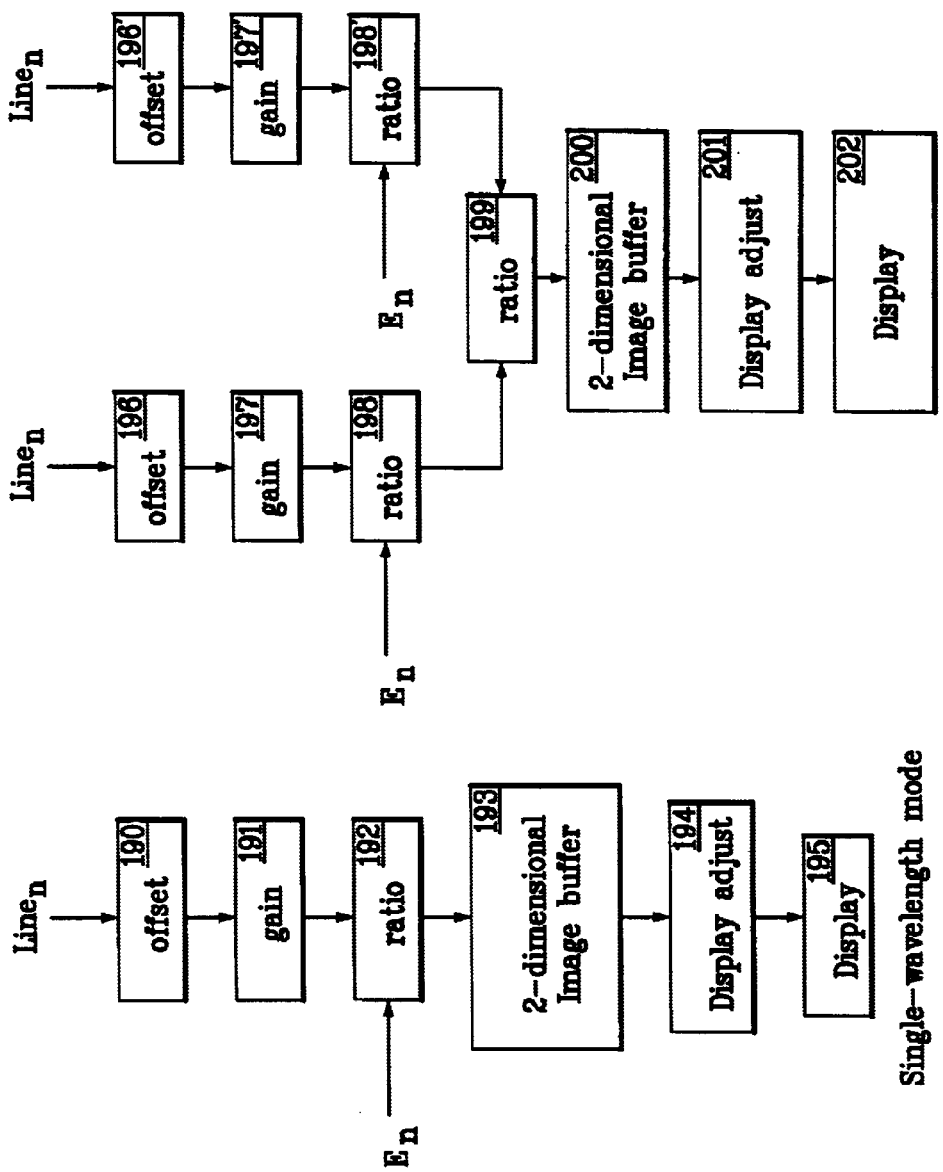
FIG. 19A is a diagram of the processing steps to be executed by the FAPS for single wavelength mode.
FIG. 19B is a diagram of the processing steps to be executed by the FAPS for differential wavelength mode.

FIG. 19A shows the processing steps to be executed by the FAPS for single wavelength mode. FIG. 19B shows the processing steps to be executed by the FAPS for differential wavelength mode. Note that in the case of 2-row illumination, a nonuniformity correction step must be inserted in the differential mode processing. For the single-wavelength mode, the energy measured at a particular line is provided with offset (190) and gain (191) and is then ratioed (192) with the detector noise-equivalent energy to produce a normalized signal. This ratio is then stored in the 2-dimensional image buffer (193). After the stored signal is provided with display adjust (194), the image is displayed (195). In the differential mode (FIG. 19B), two adjacent lines are provided offset (196, 196'), adjusted for gain (197, 197)' and ratioed (198, 198') with the detector noise-equivalent energy to produce a normalized signal and then ratioed (199). This signal is then buffered (200), given display adjust (201) and displayed (202).

Figure 20:
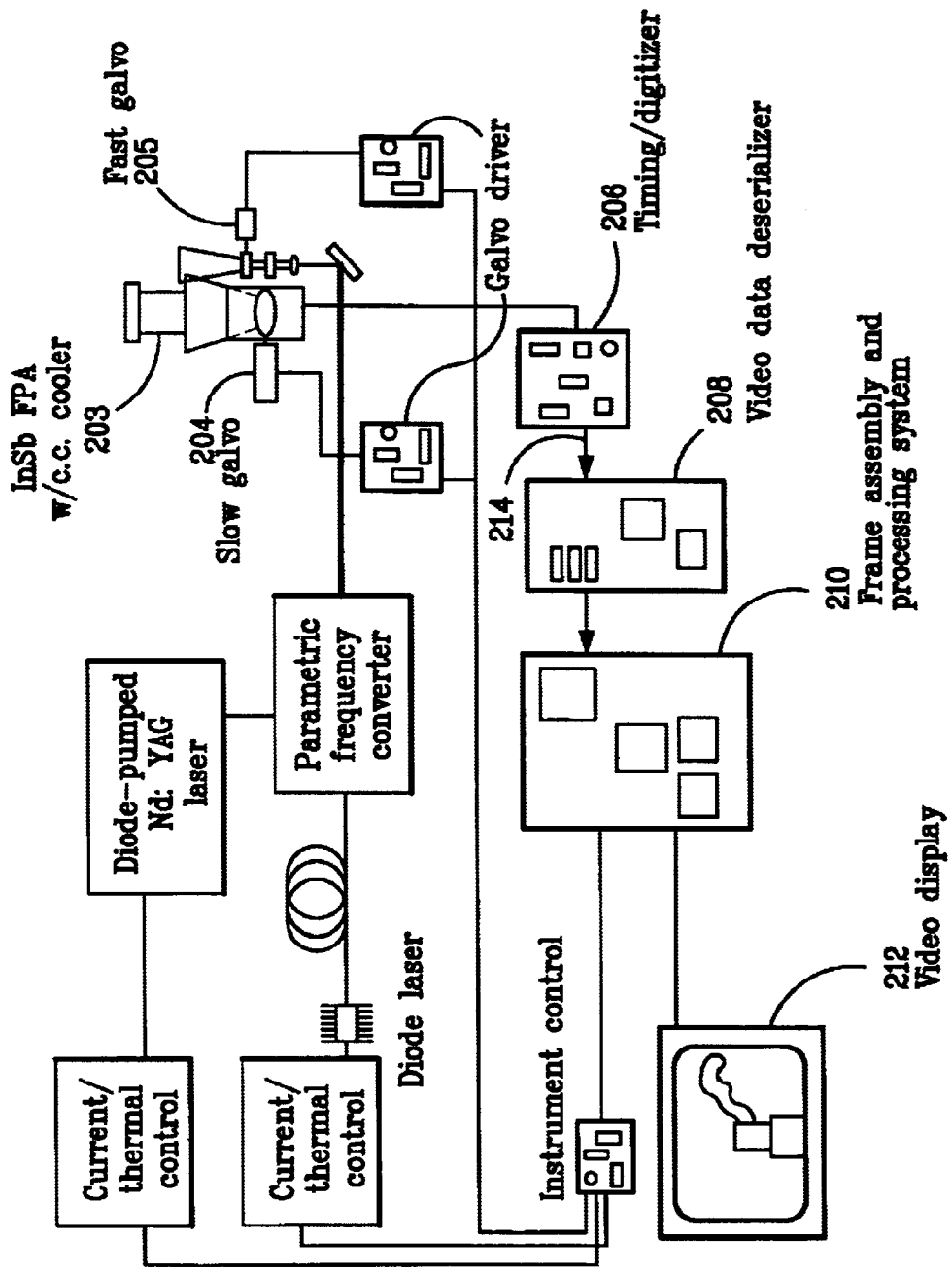
FIG. 20 provides a layout of system components.

FIG. 20 contains a diagram of an embodiment of a pulsed line scanned imager for use in portable applications. The FPA 203 is placed in a dewar with an f/1 cold stop. The camera head includes galvanometric scanners 204 and 205 and collection optics and is powered by an onboard system supply. A timing/digitizer card 206 is placed between the FPA and the deserializer card 208. Digital data is transferred directly from the deserializer card to the frame assembly and processing system (FAPS) 210, where it will be processed for differential detection and display on monitor 212. In another embodiment, the deserializer card is eliminated and digital data is transmitted to the FAPS via the high-speed serial links. The FAPS uses a dedicated processor that generates the functions illustrated in FIG. 19.

Another embodiment of the FAPS could use a dedicated processor to perform a portion or all of the necessary processing in hardware as opposed to software. The dedicated processor could consist of field programmable gate arrays, an application-specific integrated circuit, a digital signal processor, or a combination of these.

The foregoing description of the invention has been presented for purposes of illustration and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

We claim:

1. A method for imaging a gas plume, comprising:
   (i) providing pulses of light including an on-wavelength that is absorbed by a gas to be detected and an off-wavelength that is not absorbed by said gas to be detected;
   (ii) shaping said pulses into a sheet of light;
   (iii) directing said sheet of light onto a line of a target area, wherein light will be reflected and backscattered to produce a return signal;
   (iv) directing the instantaneous field-of-view (IFOV) of an imaging detector to intersect with said line of said target area that is illuminated by said sheet of light, wherein said IFOV intersects said line at an intersection zone;
   (v) imaging said return signal onto said detector;
   (vi) translating said intersection zone across said target area;
   (vii) repeating steps (i)–(vi) at various positions of said target area to create an image containing imagery of said target area and said plume of said gas to be detected.

2. The method of claim 1, wherein said light comprises electromagnetic radiation of wavelengths within the range from the ultraviolet to the infrared.

3. The method of claim 1 wherein said sheet of light comprises an illumination pattern selected from the group consisting of a linear illumination pattern and a rectangular illumination pattern.

4. The method of claim 1, wherein said intersection zone is translated at a rate sufficient to ensure that pixels in the top row of said image are well-registered with pixels at the bottom row.

5. The method of claim 4, wherein said intersection zone is translated such that said target area is completely scanned at a rate of at least 10 Hz.

6. The method of claim 1, wherein said intersection zone is translated across said target area by the motion of a platform on which said camera is contained.

7. The method of claim 1, further comprising displaying said image in real-time on a video display monitor.

8. The method of claim 1, wherein said return signal includes background signal, the method further comprising producing an image that contains only an image of said gas to be detected by removing said background by a log-ratio process.

9. The method of claim 1, further comprising calibrating said imagery of said plume of said gas to be detected to produce a quantitative measurement of concentration of said gas to be detected integrated over a path of a light pulse of said light pulses to a backscattering surface.

10. The method of claim 1, wherein each light pulse of said light pulses comprises an energy, wherein said return signal is scaled for said energy of the light pulse transmitted.

11. The method of claim 1, wherein a time between imaging of said return signal that comprises said on-wavelength and imaging of said return signal that comprises said off-wavelength is set to avoid loss of spatial registration due to motion of said camera or of said gas plume.

12. The method of claim 1, wherein step (iv) includes sweeping a single scan mirror smoothly in time to steer said intersection zone.

13. The method of claim 1, comprising adjusting the launch angle of said pulses of light from a scan mirror so that two consecutive pulses illuminate the same said line of a target area as said scan mirror moves continuously in time.

14. The method of claim 1, wherein step (iii) includes directing said sheet of light onto two lines of a target area simultaneously.

15. The method of claim 1, wherein step (iv) includes sweeping a single scan mirror in angular steps in time to steer said intersection zone.

16. The method of claim 1, wherein a first mirror translates said IFOV and a second mirror translates said sheet of light.

17. The method of claim 1, wherein said imaging detector is operated in a windowed mode in which a subset of lines in said detector are used to image backscatter from a particular light pulse, wherein said subset of lines is translated through said detector to form a complete image.

18. The method of claim 1, further comprising simultaneously measuring backscattered radiation at said on-wavelength and at said off-wavelength.

19. The method of claim 1, wherein said detector comprises a plurality of lines of detectors having pixels, wherein both said on-wavelength and said off-wavelength are imaged onto the same line of detectors of said plurality of lines of detectors to avoid errors caused by pixel nonuniformity.

20. The method of claim 1, wherein said detector comprises a plurality of lines of detectors, wherein said on-wavelength and said off-wavelength are imaged onto a different line of detectors of said plurality of lines of detectors, the method further comprising performing nonuniformity correction.

21. The method of claim 1, further comprising suppressing ambient light collected by said detector.

22. The method of claim 21 wherein the step of suppressing ambient light is carried out by a suppression method selected from the group consisting of temporal suppression, spatial suppression, and spectral suppression.

23. The method of claim 21, wherein the step of suppressing ambient light is carried out by placing a filter in front of said detector, wherein said filter transmits over a narrow spectral bandwidth centered at a wavelength being detected.

24. The method of claim 21, wherein the step of suppressing ambient light is carried out by electronically gating said detector to integrate signal for a short time window that contains the arrival time of the pulse of backscatter photons.

25. The method of claim 21, wherein the step of suppressing ambient light is carried out by limiting the dwell time of said IFOV o n a particular region of said target area.

26. A pulsed linescanner (PLS), comprising:
a lightsource that is capable of providing (i) a pulsed light beam at a wavelength that is absorbed by a gas to be detected and (ii) a pulsed light beam at a wavelength that is not absorbed by a gas to be detected;
optics for shaping said pulsed light beam into a sheet of light;
a detector; and
imaging optics for imaging said sheet of light onto said detector.

27. The PLS of claim 26, wherein said detector comprises a focal plane array (FPA) having a field-of-view that overlaps said pulsed light sheet on a target.

28. The PLS of claim 26, wherein said imaging optics comprise at least one galvanometrically-driven optic and control electronics, wherein said at least one galvanometrically driven optic is positioned to simultaneously scan said pulsed light beam and said field of view.

29. The PLS of claim 26, wherein said at least one lightsource is configured to provide pulses that alternate between said pulsed light beam at a wavelength that is absorbed by a gas to be detected and said pulsed light beam at a wavelength that is not absorbed by a gas to be detected.

30. The PLS of claim 26, wherein said at least one lightsource is selected from a group consisting of a seeded optical parametric device and an unseeded optical parametric device.

31. The PLS of claim 27, wherein said FPA is selected from the group consisting of a linear array and a 2-dimensional array with windowing.

32. The PLS of claim 26, wherein said optics for shaping said pulsed light beam into a sheet of light comprises a pair of anamorphic cylindrical projection lenses that will spread the beam as a line onto a target.

33. The PLS of claim 26, wherein said optics for shaping said pulsed light beam into a sheet of light comprises a mixing rod and a pair of cylindrical optics, wherein said mixing rod is operatively positioned to homogenize said beam into a uniform rectangular illumination, present at the exit face of said rod, wherein said exit face is then projected onto a target with the appropriate anamorphic magnification by said pair of cylindrical optics.

34. The PLS of claim 26, wherein said optics for shaping said pulsed light beam into a sheet of light comprises a multifaceted projection optic and a pair of cylindrical optics, wherein said multifaceted projection optic is operatively positioned to homogenize said beam and project it as a uniform rectangle that is then imaged onto a target by said cylindrical optics.

35. The PLS of claim 26, wherein said optics for shaping said pulsed light beam into a sheet of light are selected from the group consisting of a quasi-phasematched frequency conversion device and an amplifier with laterally patterned periodic poling that produces a flat-toped output beam from a Gaussian input beam.

36. The PLS of claim 26, wherein said optics for shaping said pulsed light beam into a sheet of light comprise an aspherical optical system to convert a Gaussian input beam to a flat-top output beam.

37. The PLS of claim 26, wherein said optics for shaping said pulsed light beam into a sheet of light comprise a diffractive optic to convert a Gaussian input beam to a flat-top output beam.

38. An apparatus for imaging a gas plume, comprising:
- a lightsource for providing pulses of light including an on-wavelength that is absorbed by a gas to be detected and an off-wavelength that is not absorbed by said gas to be detected;
- optics for shaping said pulses into a sheet of light and for directing said sheet of light onto a line of a target area, wherein light will be reflected and backscattered to produce a return signal;
- a detector having an instantaneous field-of-view (IFOV);
- optics for directing said IFOV to intersect with said line of said target area that is illuminated by said sheet of light, wherein said IFOV intersects said line at an intersection zone;
- imaging optics for imaging said return signal onto said detector; and
- a linescanner for translating said sheet of light and said IFOV such that said intersection zone translates across said target area.

39. A method for imaging a gas plume, comprising:
(i) providing pulses of light at an on-wavelength that is absorbed by a gas to be detected;
(ii) shaping said pulses into a sheet of light;
(iii) directing said sheet of light onto a line of a target area, wherein light will be reflected and backscattered to produce a return signal;
(iv) directing the instantaneous field-of-view (IFOV) of an imaging detector to intersect with said line of said target area that is illuminated by said sheet of light, wherein said IFOV intersects said line at an intersection zone;
(v) imaging said return signal onto said detector;
(vi) translating said sheet of light and said IFOV such that said intersection zone translates across said target area;
(vii) repeating steps (i)–(vi) at various positions of said target area to create an image containing imagery of said target area and imagery of said plume of said gas to be detected.

* * * * *